(12) United States Patent
Kuriyama

(10) Patent No.: US 9,521,330 B2
(45) Date of Patent: Dec. 13, 2016

(54) ENDOSCOPIC IMAGE PROCESSING DEVICE, INFORMATION STORAGE DEVICE AND IMAGE PROCESSING METHOD

(71) Applicant: OLYMPUS CORPORATION, Tokyo (JP)

(72) Inventor: Naoya Kuriyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 841 days.

(21) Appl. No.: 13/907,244

(22) Filed: May 31, 2013

(65) Prior Publication Data

US 2013/0258080 A1 Oct. 3, 2013

Related U.S. Application Data

(63) Continuation of application No. PCT/JP2011/077122, filed on Nov. 25, 2011.

(30) Foreign Application Priority Data

Dec. 2, 2010 (JP) .................................. 2010-269319

(51) Int. Cl.
*A62B 1/04* (2006.01)
*H04N 5/232* (2006.01)
(Continued)

(52) U.S. Cl.
CPC ......... *H04N 5/23296* (2013.01); *A61B 1/0005* (2013.01); *A61B 1/00009* (2013.01);
(Continued)

(58) Field of Classification Search
CPC ............ H04N 5/23296; A61B 1/00009; A61B 1/0005; A61B 1/00188
See application file for complete search history.

(56) References Cited

U.S. PATENT DOCUMENTS 5,220,647 A 6/1993 Kumagai
5,694,487 A 12/1997 Lee
(Continued)

FOREIGN PATENT DOCUMENTS

JP 05-337077 A 12/1993
JP 11-064236 A 3/1999
(Continued)

OTHER PUBLICATIONS

International Search Report dated Dec. 27, 2011 issued in PCT/JP2011/077122.
(Continued)

*Primary Examiner* — Tat Chio
(74) *Attorney, Agent, or Firm* — Scully, Scott, Murphy & Presser, P.C.

(57) ABSTRACT

The endoscopic image processing device includes an image acquisition section that acquires a normal observation image and a zoom observation image, the normal observation image being an image that includes an image of an object, and the zoom observation image being an image that magnifies the image of the object within an observation area that is part of the normal observation image, an attention area determination section that specifies an attention area on the zoom observation image, and a boundary setting section that detects a position of a boundary on the normal observation image that corresponds to a boundary of the attention area specified on the zoom observation image based on pixel values of the zoom observation image, and sets a boundary image at the detected position of the boundary on the normal observation image.

29 Claims, 18 Drawing Sheets

(51) Int. Cl.
*A61B 1/00* (2006.01)
*G06T 7/00* (2006.01)
(52) U.S. Cl.
CPC ........ *A61B 1/00188* (2013.01); *G06T 7/0012* (2013.01); *G06T 2207/10068* (2013.01); *G06T 2207/30092* (2013.01)

(56) References Cited

U.S. PATENT DOCUMENTS

| | | |
|---|---|---|
| 2002/0057341 A1 | 5/2002 | Tanaka |
| 2004/0105576 A1 | 6/2004 | Inomata |

FOREIGN PATENT DOCUMENTS

| | | |
|---|---|---|
| JP | 2001-188179 A | 7/2001 |
| JP | 2004-177325 A | 6/2004 |
| JP | 2006-141734 A | 6/2006 |
| JP | 2008-119025 A | 5/2008 |
| JP | 2010-034885 A | 2/2010 |

OTHER PUBLICATIONS

Extended Supplementary European Search Report dated Apr. 1, 2015 from related European Application No. 11 84 5207.7.

| REFERENCE POINT | SIZE |
|---|---|
| $(x_0, y_0)$ | $(m_0, n_0)$ |
| $(x_1, y_1)$ | $(m_1, n_1)$ |
| ⋮ | ⋮ |

ENDOSCOPIC IMAGE PROCESSING DEVICE, INFORMATION STORAGE DEVICE AND IMAGE PROCESSING METHOD

CROSS REFERENCE TO RELATED APPLICATION

This application is a continuation of International Patent Application No. PCT/JP2011/077122, having an international filing date of Nov. 25, 2011 which designated the United States, the entirety of which is incorporated herein by reference. Japanese Patent Application No. 2010-269319 filed on Dec. 2, 2010 is also incorporated herein by reference in its entirety.

BACKGROUND

The present invention relates to an endoscopic image processing device, information storage device and image processing method, and the like.

In recent years, an endoscopic image processing device has been widely used that allows the user to perform examination or diagnosis by inserting an elongated insertion section into a body cavity, and observing an internal organ or the like displayed on a monitor screen using a solid-state image sensor or the like provided at the end of the insertion section as an imaging means.

It has become possible to observe minute capillaries in the mucosal surface and the pit pattern of the stomach/large intestine along with an increase in image quality of an endoscopic image processing device, an increase in the number of pixels of a solid-state image sensor (e.g., CCD), and the development and widespread use of a zoom (magnifying) endoscope that is provided with a zooming function while maintaining an outer diameter and operability equal to those of a normal endoscope. Therefore, a micrometer-level fine structure can be observed, and the observation results have been applied to diagnosis of the lesion type, the invasion depth of cancer, and the like. The pit pattern of the large intestine or the intra-epithelial papillary capillary loop (IPCL) (i.e., microscopic blood vessel in the mucous membrane of the gullet) has been observed using such an endoscopic image processing device.

Since a final diagnosis is normally subjectively determined by the doctor when using such an endoscopic image processing device, development of an endoscopic image processing device that makes it possible to implement an objective and numerical diagnosis has been desired. For example, an endoscopic image processing device disclosed in JP-A-2006-141734 supports an objective diagnosis using the pattern feature quantity based on the relationship between the fine structure components of the mucous membrane within the image.

SUMMARY

According to one aspect of the invention, there is provided an endoscopic image processing device comprising:

an image acquisition section that acquires a normal observation image and a zoom observation image, the normal observation image being an image that includes an image of an object, and the zoom observation image being an image that magnifies the image of the object within an observation area that is part of the normal observation image;

an attention area determination section that specifies an attention area on the zoom observation image, the attention area being an area that requires attention; and a boundary setting section that detects a position of a boundary on the normal observation image that corresponds to a boundary of the attention area specified on the zoom observation image based on pixel values of the zoom observation image, and sets a boundary image at the detected position of the boundary on the normal observation image, the boundary image indicating the boundary of the attention area.

According to another aspect of the invention, there is provided a computer-readable storage device with an executable program stored thereon, wherein the program instructs a computer to perform steps of:

acquiring a normal observation image and a zoom observation image, the normal observation image being an image that includes an image of an object, and the zoom observation image being an image that magnifies the image of the object within an observation area that is part of the normal observation image;

specifying an attention area on the zoom observation image, the attention area being an area that requires attention; and detecting a position of a boundary on the normal observation image that corresponds to a boundary of the attention area specified on the zoom observation image based on pixel values of the zoom observation image, and setting a boundary image at the detected position of the boundary on the normal observation image, the boundary image indicating the boundary of the attention area.

According to another aspect of the invention, there is provided an image processing method comprising:

acquiring a not teal observation image and a zoom observation image, the normal observation image being an image that includes an image of an object, and the zoom observation image being an image that magnifies the image of the object within an observation area that is part of the normal observation image;

specifying an attention area on the zoom observation image, the attention area being an area that requires attention; and detecting a position of a boundary on the normal observation image that corresponds to a boundary of the attention area specified on the zoom observation image based on pixel values of the zoom observation image, and setting a boundary image at the detected position of the boundary on the normal observation image, the boundary image indicating the boundary of the attention area.

DESCRIPTION OF EXEMPLARY EMBODIMENTS

Figure 1:
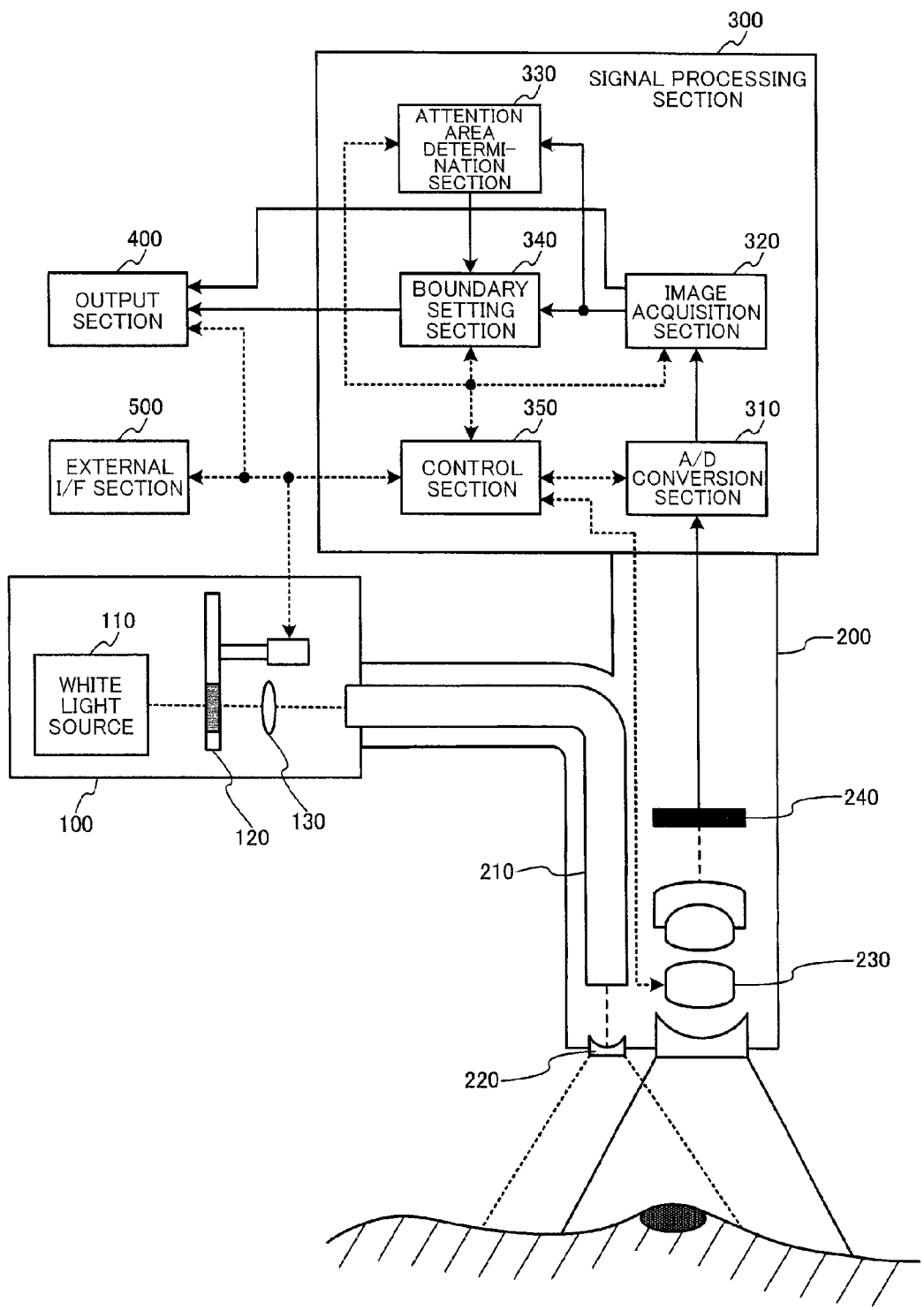
FIG. 1 illustrates a system configuration example according to one embodiment of the invention.

According to one embodiment of the invention, there is provided an endoscopic image processing device comprising:

an image acquisition section that acquires a normal observation image and a zoom observation image, the normal observation image being an image that includes an image of an object, and the zoom observation image being an image that magnifies the image of the object within an observation area that is part of the normal observation image;

an attention area determination section that specifies an attention area on the zoom observation image, the attention area being an area that requires attention; and a boundary setting section that detects a position of a boundary on the normal observation image that corresponds to a boundary of the attention area specified on the zoom observation image based on pixel values of the zoom observation image, and sets a boundary image at the detected position of the boundary on the normal observation image, the boundary image indicating the boundary of the attention area.

According to another embodiment of the invention, there is provided a computer-readable storage device with an executable program stored thereon, wherein the program instructs a computer to perform steps of:

acquiring a normal observation image and a zoom observation image, the normal observation image being an image that includes an image of an object, and the zoom observation image being an image that magnifies the image of the object within an observation area that is part of the normal observation image;

specifying an attention area on the zoom observation image, the attention area being an area that requires attention; and detecting a position of a boundary on the normal observation image that corresponds to a boundary of the attention area specified on the zoom observation image based on pixel values of the zoom observation image, and setting a boundary image at the detected position of the boundary on the normal observation image, the boundary image indicating the boundary of the attention area.

According to another embodiment of the invention, there is provided an image processing method comprising:

acquiring a normal observation image and a zoom observation image, the normal observation image being an image that includes an image of an object, and the zoom observation image being an image that magnifies the image of the object within an observation area that is part of the normal observation image;

specifying an attention area on the zoom observation image, the attention area being an area that requires attention; and detecting a position of a boundary on the normal observation image that corresponds to a boundary of the attention area specified on the zoom observation image based on pixel values of the zoom observation image, and setting a boundary image at the detected position of the boundary on the normal observation image, the boundary image indicating the boundary of the attention area.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method employed in several embodiments of the invention is described below. An endoscopic image processing device according to several embodiments of the invention includes an objective lens 230 that has a zooming function that can change the magnification of the optical system (described later). Therefore, the observation target can be observed in a normal observation mode (i.e., an observation mode at a normal magnification) and a zoom observation mode (i.e., an observation mode at a magnification higher than that of normal observation).

A normal observation image is acquired in the normal observation mode, and a zoom observation image is acquired in the zoom observation mode. The user (doctor) roughly observes a wide range or searches a lesion area using the normal observation image. The user changes the observation mode to the zoom observation mode when an attention area has been found, and closely observes the object using the zoom observation image. The user then performs procedures (e.g., excises the lesion area) in the normal observation mode using the detailed information about the object acquired from the zoom observation image.

However, a related-art endoscopic image processing device is configured so that the user must link the information acquired from the zoom observation image to the normal observation image. For example, even if the user has found the boundary between the lesion area and the normal area in the zoom observation image, the user must determine the position of the boundary in the normal observation image that is used to perform procedures (e.g., excise an area corresponding to the boundary). Therefore, the user must remember the information acquired from the zoom observation image, and perform procedures while linking the information to the normal observation image (i.e., skill is required to appropriately utilize the information presented by the endoscopic image processing device).

In order to solve the above problems, several aspects and embodiments of the invention propose an endoscopic image processing device that can smoothly link the normal observation image and the zoom observation image by presenting lesion area boundary information acquired from the zoom observation image to the user so that the lesion area boundary information is reflected in the normal observation image.

A specific method is described below taking an example illustrated in FIG. 2 in which normal observation images are acquired from a time tx to a time tx+k, zoom observation images are acquired from a time ty to a time ty+m, and normal observation images are acquired again from a time tz to a time tz+n. The link process is classified into an update process during zoom observation and a movement process during normal observation.

1.1 Update Process

The link process and the like are not performed from the time tx to the time tx+k since a zoom observation image has not been acquired. Note that the following description is given on the assumption that observation starts at the time tx. Zoom observation starts at a time ty, and information acquired from the time ty to a time ty+m is reflected in the normal observation image acquired at the time tx+k. Note that the normal observation image (reference normal observation image) in which the zoom observation results are reflected is not limited to the normal observation image acquired at the time tx+k. However, it is desirable to use the normal observation image acquired at the time tx+k immediately before the time ty taking account of the fact that it is likely that an area subjected to zoom observation is included in the preceding normal observation area.

The information acquired from the zoom observation image is reflected in the normal observation image by performing the update process illustrated in FIGS. 8A to 8D (described later). An attention area is detected from the normal observation image x+k, and an attention area boundary candidate (i.e., a candidate for the boundary between the attention area and the non-attention area) is set in advance. Note that the accuracy is lower than that during zoom observation. The attention area boundary candidate is then updated as illustrated in FIGS. 8A to 8D to determine the boundary. More specifically, when it has been determined that a non-attention area is present inside the attention area boundary candidate based on the zoom observation image, the update process is performed so that the area of the figure enclosed by the attention area boundary candidate decreases (see FIG. 8B). When it has been determined that an attention area is present outside the attention area boundary candidate based on the zoom observation image, the update process is performed so that the area of the figure enclosed by the attention area boundary candidate increases (see FIG. 8D).

1.2 Movement Process

At a time tz at which zoom observation has ended and normal observation has started again, the boundary is set based on information about a reference normal observation image (x+k) (i.e., an image that reflects the information acquired during zoom observation). More specifically, the boundary in the normal observation image x+k is moved based on motion information (i.e., information that indicates the relative motion of the object and the imaging section of the endoscope apparatus) between the time tx+k and the time tz to determine the boundary in the normal observation image z. For example, the boundary is moved by the distance between the position of the normal observation image x+k corresponding to the zoom observation image y and the position of the normal observation image x+k corresponding to the zoom observation image y+m to calculate the position of the boundary in the normal observation image z (see FIG. 16).

The boundary is moved based on the motion information about the motion between the normal observation images during a period from the time tz+1 to the time tz+n in which normal observation is continuously performed. For example, the boundary in the normal observation image z+1 acquired at the time tz+1 is set by calculating the motion information about the motion between the normal observation image z and the normal observation image z+1, and moving the boundary in the normal observation image z based on the calculated motion information.

The above description similarly applies to the subsequent process. Specifically, the update process is performed using the normal observation image z+n as the reference normal observation image when zoom observation has started after the time z+n, and the movement process is performed when normal observation has started again.

A first embodiment illustrates an example in which an attention area is automatically detected by a system, and a second embodiment illustrates an example in which an attention area is determined based on an input performed by the user.

2. First Embodiment

An endoscopic image processing device according to the first embodiment of the invention is described below with reference to FIG. 1. The endoscopic image processing device according to the first embodiment includes a light source section 100, an insertion section 200, a signal processing section 300, an output section 400, and an external I/F section 500.

The light source section 100 includes a white light source 110, a rotary filter 120, and a condenser lens 130. The white light source 110 emits white light. The rotary filter 120 is disposed to intersect the optical path of white light emitted from the white light source 110, and allows light having a specific wavelength to pass through. More specifically, the rotary filter 120 includes a normal light filter that allows three primary color lights R, $G_3$ and B to pass through, and a special light filter that allows narrow-band lights G2 and B2 to pass through, and is configured so that the filter can be switched by a rotary filter switch mechanism (not illustrated in FIG. 1). The condenser lens 130 focuses light that has passed through the rotary filter 120 on a light guide fiber 210 (described below).

The insertion section 200 is formed to be elongated and flexible (i.e., can be curved) so that the insertion section 200 can be inserted into a body cavity or the like. The insertion section 200 includes the light guide fiber 210, an illumination lens 220, the objective lens 230, and an image sensor 240. The light guide fiber 210 guides the light that has been focused by the light source section 100 to the end of the insertion section 200. The illumination lens 220 diffuses the light that has been guided by the light guide fiber 210, and applies the diffused light to the observation target. The objective lens 230 focuses reflected light from the observation target on the image sensor 240. The objective lens 230 has a zooming function that can change the magnification of the optical system. The user can change the magnification at an arbitrary timing by operating the external I/F section 500. More specifically, a control section 350 (described below) generates a control signal when the user has operated the external I/F section 500, and the objective lens 230 changes the magnification based on the control signal. The image sensor 240 outputs an analog signal based on the detected reflected light to an A/D conversion section 310 (described below).

The signal processing section 300 includes the A/D conversion section 310, an image acquisition section 320, an attention area determination section 330, a boundary setting section 340, and the control section 350. The image acquisition section 320 is connected to the attention area determination section 330, the boundary setting section 340, and the output section 400. The attention area determination section 330 is connected to the boundary setting section 340. The boundary setting section 340 is connected to the output section 400. The control section 350 is bidirectionally connected to the white light source 110, the rotary filter 120, the A/D conversion section 310, the image acquisition section 320, the attention area determination section 330, the boundary setting section 340, the output section 400, and the external I/F section 500, and controls the white light source 110, the rotary filter 120, the A/D conversion section 310, the image acquisition section 320, the attention area determination section 330, the boundary setting section 340, the output section 400, and the external I/F section 500.

The A/D conversion section 310 converts an analog signal output from the image sensor 240 into a digital signal, and outputs the digital signal to the image acquisition section 320.

The image acquisition section 320 determines whether the current observation is normal light observation or special light observation based on the control signal output from the control section 350, and performs image processing (e.g., interpolation process, white balance process, color conversion process, and grayscale transformation process) on the digital signal output from the AD conversion section 310 corresponding to the observation method to generate a normal light image or a special light image. The image acquisition section 320 determines whether the generated image is a zoom observation image acquired during zoom observation or a normal observation image acquired during normal observation based on the control signal. Specifically, the image acquired by the image acquisition section 320 has two attributes (i.e., normal light image/special light image and zoom observation image/normal observation image) corresponding to the observation state in which the image has been acquired.

Figure 2:
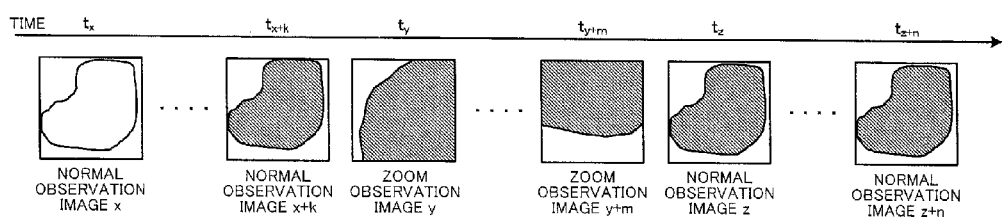
FIG. 2 is a view illustrating an example in which normal observation images and zoom observation images are acquired in time series.

FIG. 2 illustrates an example in which zoom observation images and normal observation images are successively acquired by the image acquisition section 320 in time series. In the example illustrated in FIG. 2, the image acquisition section 320 acquires a normal observation image x to a normal observation image x+k from an observation start time tx to a time tx+k, and acquires a zoom observation image y to a zoom observation image y+m from a time ty to a time ty+m. The image acquisition section 320 then acquires a normal observation image z to a normal observation image z+n from a time tz to a time tz+n. In this case, each element according to the first embodiment functions as described below. When the attention area determination section 330 has detected that zoom observation has started at the time ty based on the control signal generated by the control section 350, the attention area determination section 330 detects an attention area from the normal observation image x+k based on the pixel values of the normal observation image x+k. The attention area determination section 330 then detects an attention area from each of the zoom observation image y to the zoom observation image y+m based on the pixel values of each zoom observation image. The boundary setting section 340 sets a boundary image on the normal observation image x+k based on the attention area detected from the normal observation image x+k and the attention area detected from each of the zoom observation image y to the zoom observation image y+m during a period in which execution of zoom observation is detected based on the control signal. The attention area determination section 330 detects that zoom observation has ended at the time tz based on the control signal. When the boundary setting section 340 has detected that zoom observation has ended based on the control signal, the boundary setting section 340 sets the attention area and the boundary image on the normal observation image z based on the magnification, the moving amount between the zoom observation image y and the zoom observation image y+m, the attention area and the boundary image set on the normal observation image x+k.

The boundary setting section 340 sets the attention area and the boundary image on the normal observation image z+1 at the time tz+1 based on the moving amount between the normal observation image z and the normal observation image z+1, the attention area and the boundary image set on the normal observation image z. The boundary setting section 340 similarly sets the attention area and the boundary image on the subsequent normal observation images during a period in which execution of normal observation is detected based on the control signal. When zoom observation has started again, the boundary setting section 340 sets the attention area and the boundary image on the normal observation image acquired after zoom observation based on the attention area and the boundary image set on the normal observation image acquired immediately before zoom observation has started, and the attention area set during zoom observation.

Figure 3:
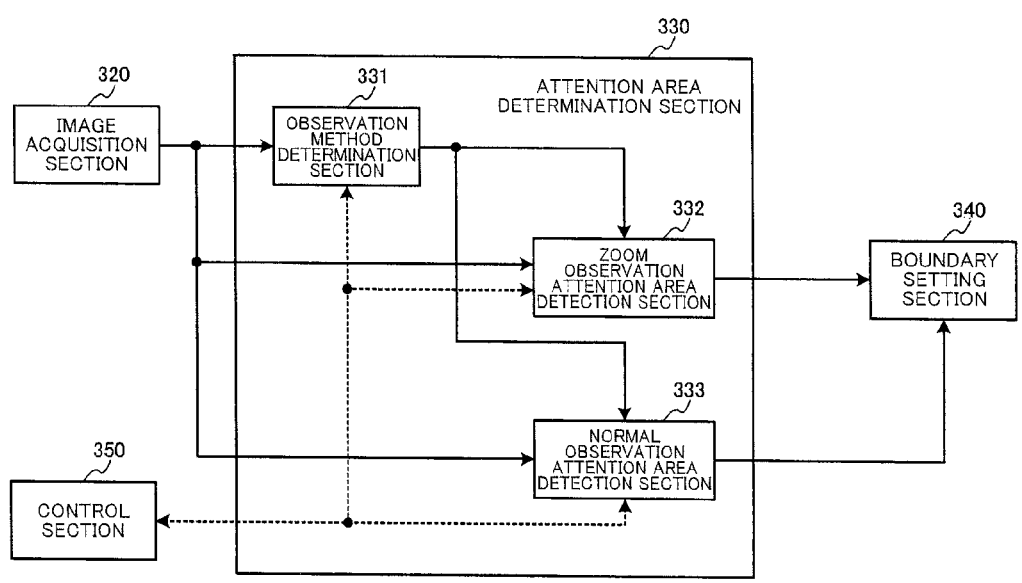
FIG. 3 illustrates a configuration example of an attention area determination section.

A specific configuration of the attention area determination section 330 is described below. FIG. 3 is a block diagram illustrating an example of the configuration of the attention area determination section 330 according to the first embodiment. As illustrated in FIG. 3, the attention area determination section 330 includes an observation method determination section 331, a zoom observation attention area detection section 332, and a normal observation attention area detection section 333. A zoom observation image acquired by the image acquisition section 320 is output to the zoom observation attention area detection section 332. A normal observation image acquired by the image acquisition section 320 is output to the observation method determination section 331 and the normal observation attention area detection section 333. The control signal generated by the control section 350 is output to the observation method determination section 331, the zoom observation attention area detection section 332, and the normal observation attention area detection section 333 to control the observation method determination section 331, the zoom observation attention area detection section 332, and the normal observation attention area detection section 333. The observation method determination section 331 is connected to the zoom observation attention area detection section 332 and the normal observation attention area detection section 333. The zoom observation attention area detection section 332 is connected to the boundary setting section 340. The normal observation attention area detection section 333 is connected to the boundary setting section 340.

The observation method determination section 331 determines whether the observation method is normal light observation or special light observation based on the control signal. When the observation method is normal light observation, the observation method determination section 331 determines whether or not the observation method utilizes a dye or a stain based on the color tone of the normal observation image. More specifically, the number of pixels of the normal observation image that have a chroma equal to or more than a given value and a hue within the range of −10° (350°) to 20° is referred to as $\alpha$, and the number of pixels of the normal observation image that have a chroma equal to or more than a given value and a hue within the range of 20° to 350° is referred to as $\beta$. The observation method determination section 331 determines that the observation method does not utilize a dye or a stain when $\alpha > 2.0 \times \beta$, and determines that the observation method utilizes a dye or a stain when $\alpha < 2.0 \times \beta$. The hue range corresponding to the number $\beta$ may be a value corresponding to a dye or a stain used for observation.

Figure 4:
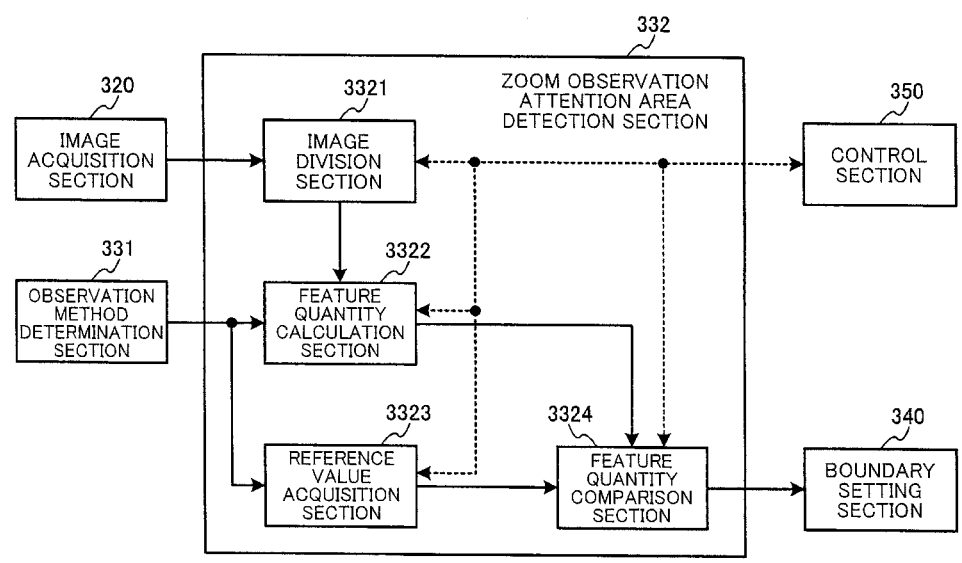
FIG. 4 illustrates a configuration example of a zoom observation attention area detection section.

A specific configuration of the zoom observation attention area detection section 332 is described below. FIG. 4 is a block diagram illustrating an example of the configuration of the zoom observation attention area detection section 332 according to the first embodiment. As illustrated in FIG. 4, the zoom observation attention area detection section 332 includes an image division section 3321, a feature quantity calculation section 3322, a reference value acquisition section 3323, and a feature quantity comparison section 3324. A zoom observation image acquired by the image acquisition section 320 is output to the image division section 3321. The information about the observation method determined by the observation method determination section 331 is output to the feature quantity calculation section 3322 and the reference value acquisition section 3323. The control signal generated by the control section 350 is output to the image division section 3321, the feature quantity calculation section 3322, the reference value acquisition section 3323, and the feature quantity comparison section 3324 to control the image division section 3321, the feature quantity calculation section 3322, the reference value acquisition section 3323, and the feature quantity comparison section 3324. The image division section 3321 is connected to the feature quantity calculation section 3322. The feature quantity calculation section 3322 is connected to the feature quantity comparison section 3324. The reference value acquisition section 3323 is connected to the feature quantity comparison section 3324. The feature quantity comparison section 3324 is connected to the boundary setting section 340.

Figure 5:
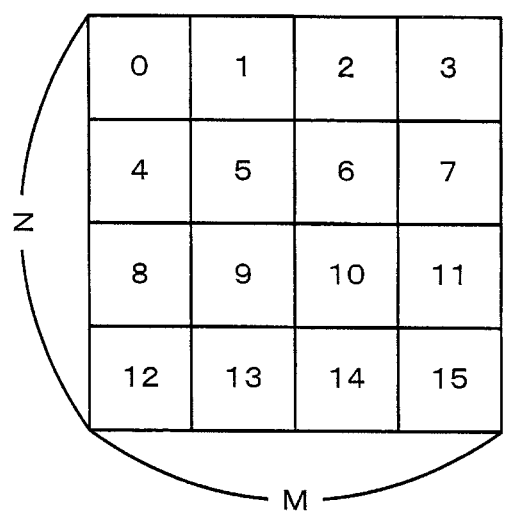
FIG. 5 illustrates an example of block division implemented by an image division section.

The image division section 3321 divides the zoom observation image into a plurality of block images. For example, the image division section 3321 divides the zoom observation image having a size of M×N into sixteen block images (size: (M/4)×(N/4)) in the horizontal direction and the vertical direction (see FIG. 5). The boundary between the attention area and the non-attention area can be accurately set by thus dividing the zoom observation image, and calculating the feature quantity (described below) on a block image basis.

The feature quantity calculation section 3322 calculates the feature quantity corresponding to the observation method determined by the observation method determination section 331 on a block image basis (i.e., corresponding to each block image obtained by the image division section 3321). For example, when the observation method is special light observation, the feature quantity calculation section 3322 calculates the feature quantity based on the IPCL pattern that is considered to be useful for diagnosis of the invasion depth of cancer during zoom observation. When the observation method is normal observation, the feature quantity calculation section 3322 calculates the feature quantity based on the pit pattern described in JP-A-2006-141734. Note that a different threshold value is used for the binarization process described in paragraph [0021] of JP-A-2006-141734 depending on whether or not the observation method utilizes a dye or a stain.

The reference value acquisition section 3323 stores the typical feature quantity at each invasion depth of cancer as a reference value corresponding to each observation method, and acquires the reference value corresponding to the observation method. The feature quantity corresponding to the observation method is calculated in advance from a known lesion image for which the invasion depth can be clearly determined, and used as the reference value. The reference value acquisition section 3323 acquires the reference value corresponding to the observation method determined by the observation method determination section 331.

The feature quantity comparison section 3324 compares the feature quantity with the reference value on a block image basis to determine whether or not the block image is a zoom observation attention area. More specifically, the feature quantity comparison section 3324 calculates the difference between the feature quantity and the reference value, and determines that the block image is a zoom observation attention area when the difference is equal to or less than a given threshold value. The information about the zoom observation attention area is output to the boundary setting section 340.

The normal observation attention area detection section 333 detects the attention area based on the pixel values of the normal observation image using a method corresponding to the observation method determined by the observation method determination section 331. More specifically, when the observation method determination section 331 has determined that the observation method is special light observation, the normal observation attention area detection section 333 sets an area in which the hue of each pixel is 5° to 35° and which has an area equal to or more than a given value as a normal observation attention area, for example. This is because the IPCL is observed as a brown area referred to as "brown spot" during normal observation using special light. Note that the user may set the normal observation attention area when the observation method determination section 331 has determined that the observation method is normal light observation. When the user does not set the normal observation attention area, an area in which the R channel of the pixel value is equal to or more than a threshold value and which is closest to the center of the image is set on the normal observation image as the normal observation attention area, for example. In the first embodiment, the normal observation attention area detection section 333 always sets the normal observation attention area on the normal observation image. Note that the normal observation attention area detection section 333 may set the normal observation attention area on only the normal observation image that has been output at a time at which it has been detected that normal observation has ended based on the control signal. The normal observation attention area detection section 333 may set the normal observation attention area on only the normnal observation image for which the boundary image has not been set.

Figure 6:
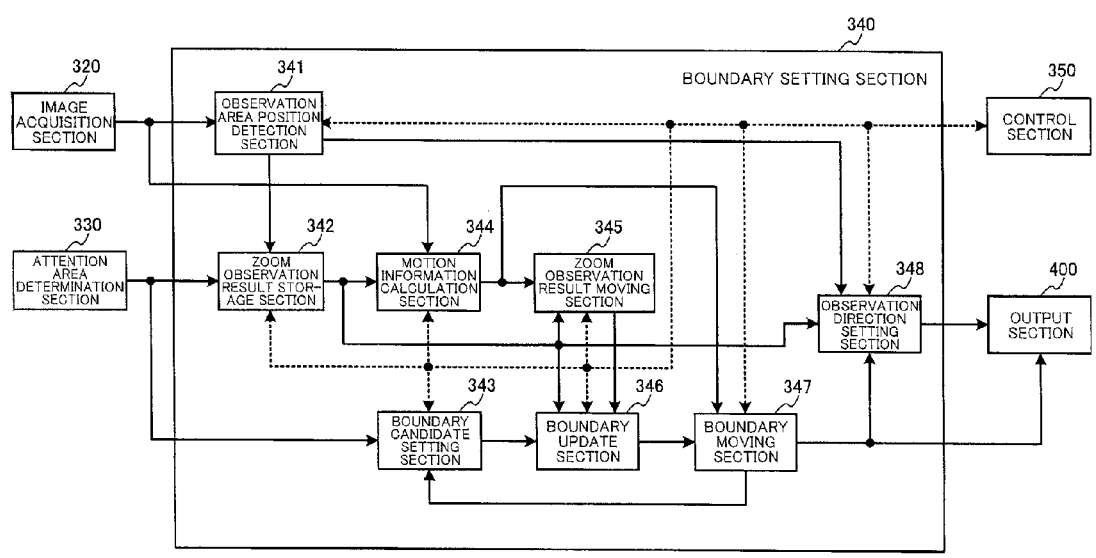
FIG. 6 illustrates a configuration example of a boundary setting section.

A specific configuration of the boundary setting section 340 is described below. FIG. 6 is a block diagram illustrating an example of the configuration of the boundary setting section 340 according to the first embodiment. As illustrated in FIG. 6, the boundary setting section 340 includes an observation area position detection section 341, a zoom observation result storage section 342, a boundary candidate setting section 343, a motion information calculation section 344, a zoom observation result moving section 345, a boundary update section 346, a boundary moving section 347, and an observation direction setting section 348.

A zoom observation image acquired by the image acquisition section 320 is output to the observation area position detection section 341. A normal observation image acquired by the image acquisition section 320 is output to the observation area position detection section 341 and the motion information calculation section 344. A zoom observation attention area detected by the attention area determination section 330 is output to the zoom observation result storage section 342. A normal observation attention area detected by the attention area determination section 330 is output to the boundary candidate setting section 343. The control signal generated by the control section 350 is output to the observation area position detection section 341, the zoom observation result storage section 342, the boundary candidate setting section 343, the motion information calculation section 344, the zoom observation result moving section 345, the boundary update section 346, the boundary moving section 347, and the observation direction setting section 348 to control the observation area position detection section 341, the zoom observation result storage section 342, the boundary candidate setting section 343, the motion information calculation section 344, the zoom observation result moving section 345, the boundary update section 346, the boundary moving section 347, and the observation direction setting section 348. The observation area position detection section 341 is connected to the zoom observation result storage section 342 and the observation direction setting section 348. The zoom observation result storage section 342 is connected to the motion information calculation section 344, the zoom observation result moving section 345, the boundary update section 346, and the observation direction setting section 348. The boundary candidate setting section 343 is connected to the boundary update section 346. The motion information calculation section 344 is connected to the zoom observation result moving section 345 and the boundary moving section 347. The zoom observation result moving section 345 is connected to the boundary update section 346. The boundary update section 346 is connected to the boundary moving section 347 and the observation direction setting section 348. The boundary moving section 347 is connected to the boundary candidate setting section 343 and the output section 400. The observation direction setting section 348 is connected to the output section 400.

When the observation area position detection section 341 has detected that zoom observation has started based on the control signal, the observation area position detection section 341 stores the normal observation image acquired at the time immediately before the current time as a reference normal observation image, and detects the position of the reference normal observation image that is subjected to zoom observation in each zoom observation image acquired until it is detected that zoom observation has ended based on the control signal. More specifically, the observation area position detection section 341 performs a known image matching process on the reference normal observation image and the zoom observation image for which the resolution is reduced corresponding to the magnification, and detects the coordinates on the reference normal observation image that correspond to the center of the zoom observation image as the observation area position. When the image acquired immediately before the zoom observation image (e.g., the zoom observation image y+1 illustrated in FIG. 2 that is acquired at the time ty+1) is also a zoom observation image (e.g., the zoom observation image y illustrated in FIG. 2), the observation area position detection section 341 performs the image matching process in a state in which the observation area position detected from the zoom observation image y coincides with the center of the zoom observation image y+1 for which the resolution is reduced, and detects the observation area position of the zoom observation image y+1 on the reference normal observation image. When the image acquired immediately before the zoom observation image (e.g., the zoom observation image y illustrated in FIG. 2) is a normal observation image (e.g., the normal observation image x+k illustrated in FIG. 2), the observation area position detection section 341 performs the image matching process in a state in which the center of the reference normal observation image coincides with the center of the zoom observation image y for which the resolution is reduced, and detects the observation area position of the zoom observation image y on the reference normal observation image. The observation area position detection section 341 outputs the reference normal observation image to the zoom observation result storage section 342 when the observation area position detection section 341 has detected that zoom observation has started. The observation area position detection section 341 outputs the observation area position to the zoom observation result storage section 342 until the observation area position detection section 341 detects that zoom observation has ended. The observation area position detection section 341 also outputs the observation area position detected when zoom observation has started, and the observation area position detected when zoom observation has ended, to the zoom observation result storage section 342 as a zoom start position and a zoom end position, respectively.

The zoom observation result storage section 342 stores the information that has been output from the observation area position detection section 341, and indicates the area of the reference normal observation image that is subjected to zoom observation, and the area that has been determined to be the attention area as a result of zoom observation. More specifically, the zoom observation result storage section 342 stores the area obtained by reducing the zoom observation attention area in the zoom observation image by a magnification Z around the observation area position as the attention area (zoom observation result), and stores the area having a size of (M/Z)×(N/Z) around the observation area position as a zoom observation completion area (zoom observation result). Note that the size of the image is M×N. The zoom observation result storage section 342 stores the zoom start position output from the observation area position detection section 341 until the zoom end position is output, and outputs the zoom start position and the zoom end position to the motion information calculation section 344 when the zoom end position has been output.

Figure 7A:
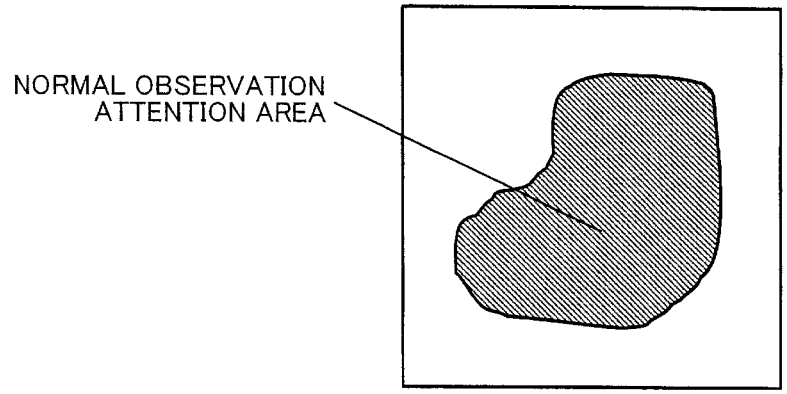
FIGS. 7A to 7C are views illustrating a method that sets control points along the boundary of a normal observation attention area, and calculates an attention area boundary candidate.
Figure 7B:
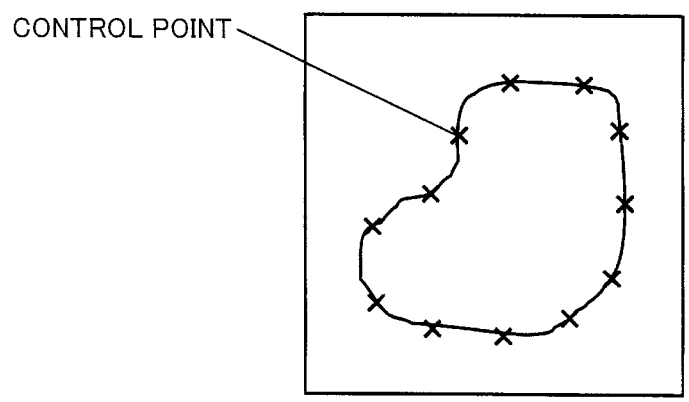
Figure 7C:
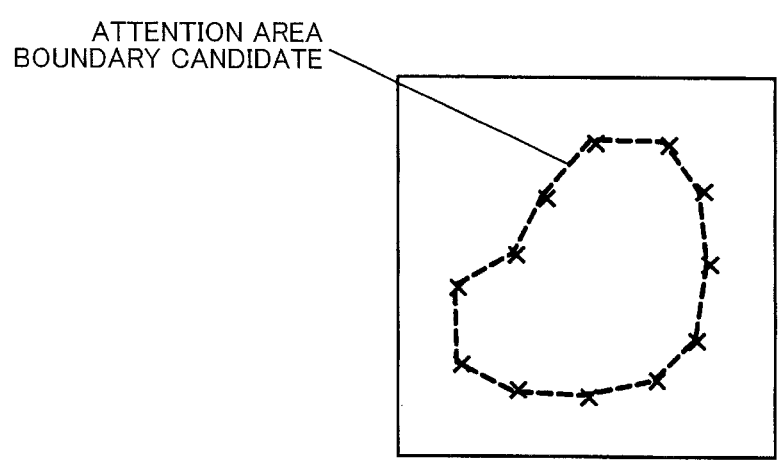
Figure 8A:
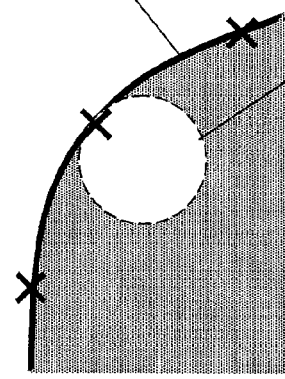
FIGS. 8A to 8D are views illustrating an example in which a boundary image on a normal observation image is updated based on the results of zoom observation.
Figure 8B:
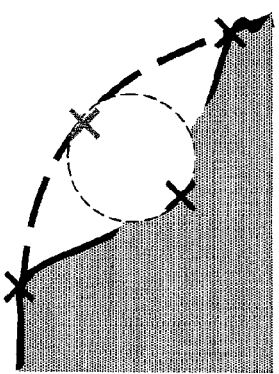
Figure 8C:
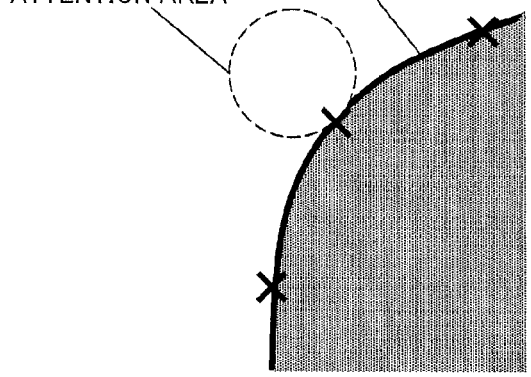
Figure 8D:
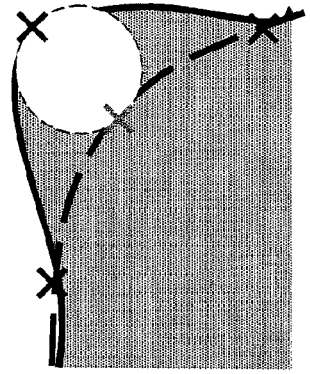

The boundary candidate setting section 343 sets the boundary image as a boundary image candidate when the boundary moving section 347 has moved the boundary image on the normal observation image (i.e., when a boundary that reflects the zoom observation results has been set). When the boundary moving section 347 has not moved the boundary image on the normal observation image, the boundary candidate setting section 343 sets the contour of the normal observation attention area as the boundary image candidate. More specifically, the boundary candidate setting section 343 detects the contour of the normal observation attention area (see FIG. 7A). The boundary candidate setting section 343 then determines the number Np of control points corresponding to the number Nc of pixels that form the contour. For example, Np=Nc/10. The boundary candidate setting section 343 then extracts Np pixels (i.e., control points) from the pixels that form the contour at equal intervals (see FIG. 7B). The boundary candidate setting section 343 sets an Np-gonal area obtained by connecting the control points by a line segment as the boundary image candidate (see FIG. 7C).

The motion information calculation section 344 calculates the moving amount between two normal observation images. For example, when only zoom observation is performed during a period between the acquisition time of the normal observation image x+k and the acquisition time of the normal observation image z (see FIG. 2), the moving amount is the difference between the observation area position Py that is output from the zoom observation result storage section 342 as the zoom start position and has been detected by the observation area position detection section 341 from the zoom observation image y (see FIG. 2), and the observation area position Py+m that is output from the zoom observation result storage section 342 as the zoom end position and has been detected by the observation area position detection section 341 from the zoom observation image y+m (see FIG. 2). When only normal observation is performed during a period between the acquisition time of the normal observation image z and the acquisition time of the normal observation image z+1 (see FIG. 2), the moving amount is calculated by a known method (e.g., image matching process) based on the nomial observation image z and the normal observation image z+1. When both zoom observation and normal observation are performed during a period between the acquisition times of two normal observation images for which the moving amount is calculated, the images acquired during a period between the acquisition times of the two normal observation images for which the moving amount is calculated are classified into a zoom observation image section and a normal observation image section, and the moving amount in each section calculated as described above is summed up.

The zoom observation result moving section 345 moves the zoom observation results during normal observation based on the moving amount. More specifically, the zoom observation result moving section 345 moves the zoom observation completion area and the attention area stored as the zoom observation results based on the moving amount. This makes it possible to utilize the previous zoom observation results when performing not mal observation subsequent to zoom observation, and then performing zoom observation again.

The boundary update section 346 sets the boundary image during zoom observation based on the zoom observation results stored in the zoom observation result storage section 342, the zoom observation results output from the zoom observation result moving section 345, and the boundary image candidate set by the boundary candidate setting section 343. More specifically, the boundary update section 346 updates the boundary image candidate depending on whether or not the vicinity of the control points that form the boundary image candidate is the attention area. The boundary image candidate is updated as described below. The boundary image candidate is indicated by Np control points. Each control point is indicated by a two-dimensional vector pi. Note that pi−1 and pi and pi and pi+1 indicate adjacent control points, i=0 to Np−1, and p0=pNp. The suffix i of the control point is assigned so that the suffix i increases clockwise along the contour of the boundary image. The control point pi is updated to pi' using the following expression.

$$p'_i = p_i + \alpha T \frac{(p_{i+1} - p_{i-1})}{|p_{i+1} - p_{i-1}|} \tag{1}$$

$$T = \begin{pmatrix} 0 & -1 \\ 1 & 0 \end{pmatrix}$$

$$p_i = \begin{pmatrix} x_i \\ y_i \end{pmatrix}$$

$\alpha$ is a coefficient that indicates the magnitude and the direction of update of the control point. When the absolute value of $\alpha$ is large, the control point is updated to a large extent. When $\alpha$>0, the control point is updated in the direction in which the area of the boundary image increases. When $\alpha$<0, the control point is updated in the direction in which the area of the boundary image decreases. For example, $\alpha$=±10. When one or more control points have been updated, all of the control points are updated so that the distance between adjacent control points is equal.

The boundary image candidate or the boundary image is updated under the following conditions. When the observation area position that is inscribed to the boundary image candidate is not the zoom observation attention area (see FIG. 8A), $\alpha$ is set to −10 so that the area of the boundary image candidate decreases, and the boundary image candidate is updated around the observation area position (see FIG. 8B), and used as the boundary image. When the observation area position that is circumscribed to the boundary image candidate is the zoom observation attention area (see FIG. 8C), $\alpha$ is set to +10 so that the area of the boundary image candidate increases, and the boundary image candidate is updated around the observation area position (see FIG. 8D), and used as the boundary image. The boundary image is then similarly updated based on the zoom observation results.

The boundary moving section 347 moves the boundary image updated by the boundary update section 346 based on the moving amount calculated by the motion information calculation section 344 during normal observation. More specifically, the boundary moving section 347 moves the coordinates of the control points that form the boundary image based on the moving amount. This makes it possible to track the boundary image set during zoom observation even if the endoscope has moved during normal observation. When the coordinates of all of the control points have moved to the outside of the normal observation image due to the movement of the endoscope, and moved away from the normal observation image by a given distance or more, the boundary moving section 347 deletes the boundary image.

Figure 9:
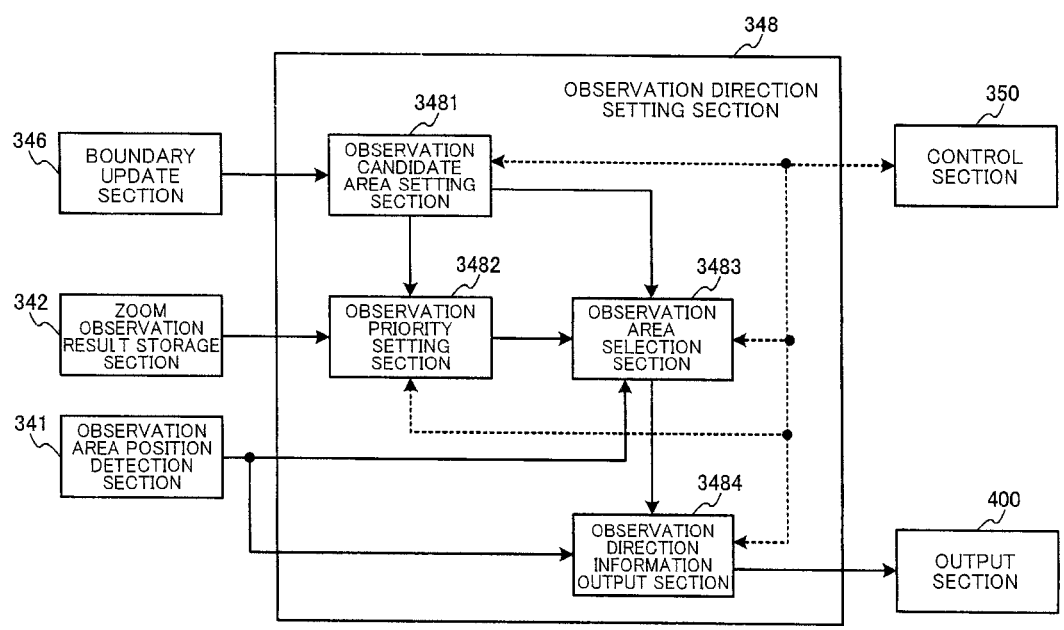
FIG. 9 illustrates a configuration example of an observation direction setting section.

The observation direction setting section 348 starts operation when the observation direction setting section 348 has detected that zoom observation has started based on the control signal, sets information about the next observation target direction, and outputs the information to the output section 400. A specific configuration of the observation direction setting section 348 is described below. FIG. 9 is a block diagram illustrating an example of the configuration of the observation direction setting section 348 according to the first embodiment. As illustrated in FIG. 9, the observation direction setting section 348 includes an observation candidate area setting section 3481, an observation priority setting section 3482, an observation area selection section 3483, and an observation direction information output section 3484.

The boundary image updated by the boundary update section 346 is output to the observation candidate area setting section 3481. The zoom observation results stored in the zoom observation result storage section 342 are output to the observation priority setting section 3482. The observation area position detected by the observation area position detection section 341 is output to the observation area selection section 3483 and the observation direction information output section 3484. The control signal generated by the control section 350 is output to the observation candidate area setting section 3481, the observation priority setting section 3482, the observation area selection section 3483, and the observation direction information output section 3484 to control the observation candidate area setting section 3481, the observation priority setting section 3482, the observation area selection section 3483, and the observation direction information output section 3484. The observation candidate area setting section 3481 is connected to the observation priority setting section 3482 and the observation area selection section 3483. The observation priority setting section 3482 is connected to the observation area selection section 3483. The observation area selection section 3483 is connected to the observation direction information output section 3484. The observation direction information output section 3484 is connected to the output section 400.

The observation candidate area setting section 3481 sets a candidate for the observation target area on the boundary image as an observation candidate area. More specifically, the observation candidate area setting section 3481 sets the observation candidate areas on the boundary image at constant intervals. For example, the observation candidate area is set around the control points that form the boundary image (see FIG. 10). When the size of the observation candidate area in the vertical direction is LM, and the size of the observation candidate area in the horizontal direction is LN, the size of the observation candidate area is determined by the following expressions using the size (M and N) of the block image and the magnification Z.

$$LM = M/Z \quad (2)$$

$$LN = N/Z \quad (3)$$

Figure 10:
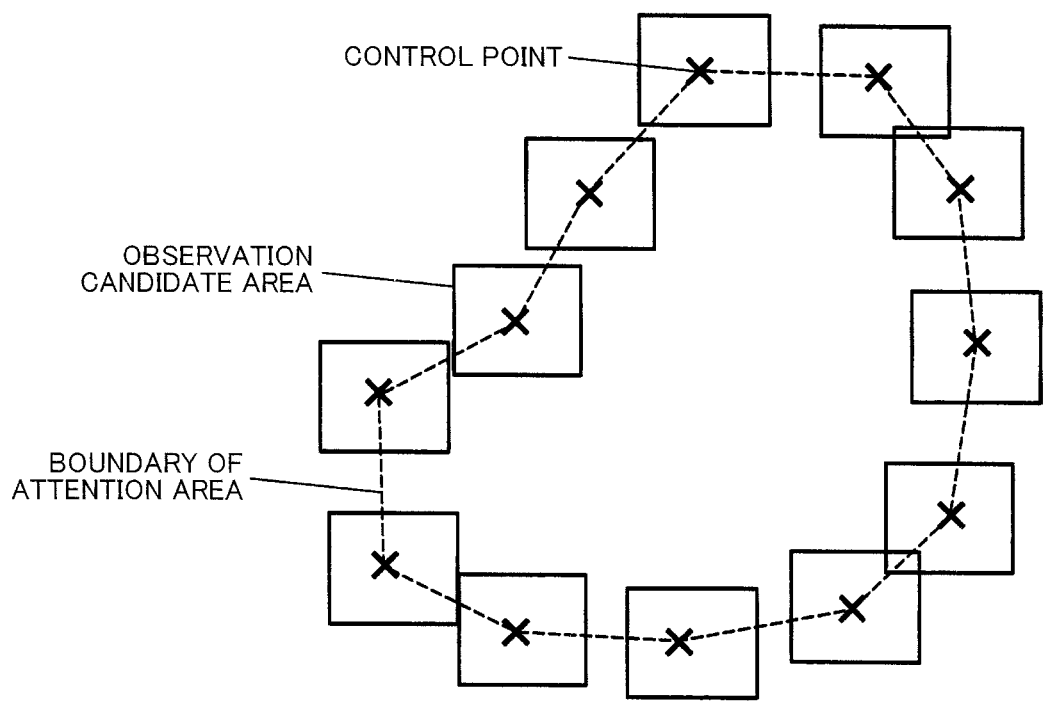
FIG. 10 illustrates an observation candidate area setting example.

In FIG. 10, the observation candidate area is set to have a rectangular shape. Note that the observation candidate area may be set to have a circular shape, an elliptical shape, or the like.

Figure 11:
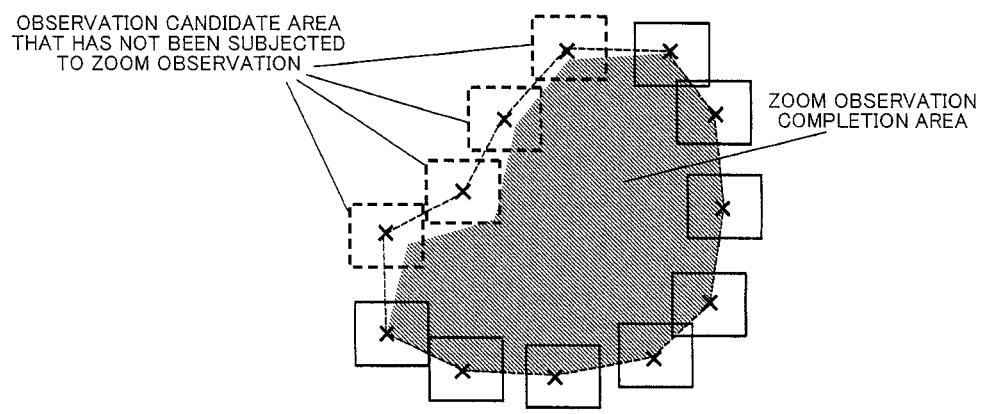
FIG. 11 is a view illustrating an observation candidate area that has not been subjected to zoom observation.

The observation priority setting section 3482 sets observation priority to the observation candidate area based on the boundary image and the zoom observation results. More specifically, the observation priority setting section 3482 determines whether or not each observation candidate area has been subjected to zoom observation based on the zoom observation completion area stored as the zoom observation result, and sets the observation priority to the observation candidate area that has not been subjected to zoom observation. The observation priority setting section 3482 does not set the observation priority to the observation candidate area that has been subjected to zoom observation since further zoom observation is unnecessary. For example, the observation priority setting section 3482 determines that the observation candidate area that is included in the zoom observation completion area by less than 30% of the total area has not been subjected to zoom observation (see FIG. 11), and sets the observation priority to the observation candidate area. When a plurality of (N) observation candidate areas have not been subjected to zoom observation, the minimum distance from the zoom observation completion area to each observation candidate area is used as a first observation priority determination index, and first observation priority is set (1, 2, 3, . . . , N) to the observation candidate areas in descending order of the first observation priority determination index. A smaller first observation priority value indicates that the observation candidate area should be observed with higher priority. When a plurality of observation candidate areas have an identical first observation priority determination index, the first observation priority determination indices of the plurality of observation candidate areas are compared after adding the first observation priority determination index of the adjacent observation candidate area, and higher first observation priority is set to the observation candidate area having a larger observation priority determination index.

The observation area selection section 3483 selects the next observation target observation candidate area during zoom observation. More specifically, the observation area selection section 3483 selects the observation candidate area that is given higher first observation priority and positioned near the observation area position at which zoom observation is currently performed. For example, when N observation candidate areas are present, and the first observation priority has been assigned up to N, second observation priority is assigned to the observation candidate areas up to N in ascending order of the distance from the observation area position to the center of the observation candidate area, and the observation candidate area for which the sum of the first observation priority and the second observation priority is smallest is selected. For example, when the first observation priority is $xi$ ($xi=1$ to N, suffix that identifies observation candidate area, $i=1$ to N), and the second observation priority is $yi$ ($yi=1$ to N, i: suffix that identifies observation candidate area, $i=1$ to N), the value $xi+yi$ is calculated for each observation candidate area, and the observation candidate area for which the value $xi+yi$ is smallest is selected.

Figure 12:
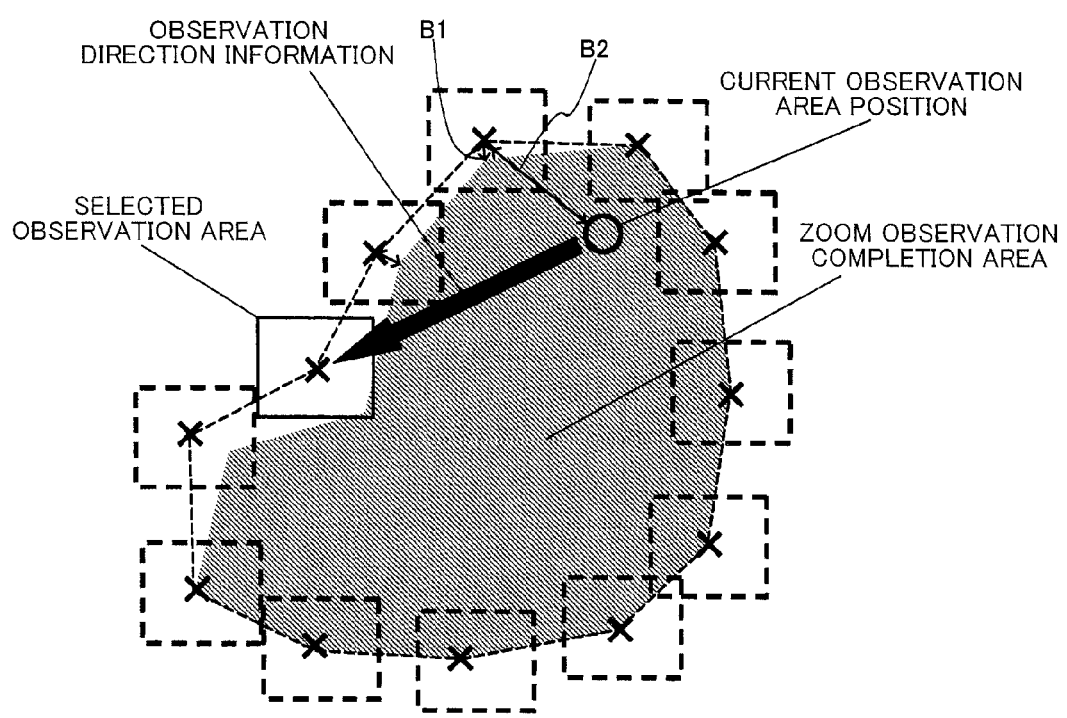
FIG. 12 illustrates an example of observation priority and observation direction information.

The observation direction information output section 3484 outputs direction information about the next observation target direction based on the position of the observation candidate area selected by the observation area selection section 3483 and the observation area position at which zoom observation is currently performed (see FIG. 12). More specifically, when the position of the selected observation candidate area is indicated by a two-dimensional vector s, and the observation area position at which zoom observation is currently performed is indicated by a two-dimensional vector t, the observation target direction d is expressed by the following expression.

$$d = \frac{s-t}{|s-t|} \quad (4)$$

For example, the output section 400 outputs an arrow corresponding to the direction d as the direction information. The size of the arrow may be linked to the distance $|s-t|$ between the position of the selected observation candidate area and the observation area position at which zoom observation is currently performed. The color density of the arrow may be changed corresponding to the distance $|s-t|$. For example, the arrow is displayed at the maximum color density when the distance $|s-t|$ is equal to or longer than a given value, and the color density is reduced as the distance from the selected observation candidate area decreases. The display of the arrow is stopped when the selected observation candidate area has been subjected to zoom observation. When another observation candidate area has been selected by the observation area selection section 3483, an arrow that indicates the direction information about the direction toward the selected observation candidate area is displayed. When each observation candidate area has been subjected to zoom observation, the output section 400 outputs information to that effect.

The control section 350 is connected to the white light source 110, the rotary filter 120, the A/D conversion section 310, the image acquisition section 320, the attention area determination section 330, the boundary setting section 340, the output section 400, and the external I/F section 500, and outputs the control signal that controls the white light source 110, the rotary filter 120, the A/D conversion section 310, the image acquisition section 320, the attention area determination section 330, the boundary setting section 340, the output section 400, and the external I/F section 500.

The output section 400 outputs the normal observation image or the zoom observation image acquired by the image acquisition section 320. The output section 400 is an image display device (e.g., endoscope monitor), for example. When the output section 400 has detected that normal observation has started based on the control signal, the output section 400 displays the boundary image set by the boundary setting section 340 on the normal observation image. For example, the output section 400 displays the contour of the boundary image on the normal observation image. The inner area of the boundary image may be displayed on the normal observation image as a translucent mask. When the output section 400 has detected that zoom observation has started based on the control signal, the output section 400 displays the direction information set by the boundary setting section 340 on the endoscope monitor. When the boundary setting section 340 has output information that indicates that each observation candidate area has been subjected to zoom observation, the output section 400 displays information (e.g., text information) to that effect on the endoscope monitor.

The external I/F section 500 is an interface that allows the user to perform an input operation or the like on the image processing device. The external I/F section 500 includes a power switch (power ON/OFF switch), a shutter button (imaging operation start button), a mode (e.g., imaging mode) change button, and the like.

According to the first embodiment, the endoscopic image processing device includes the image acquisition section 320 that acquires a noiinal observation image and a zoom observation image, the attention area determination section 330 that specifies an attention area on the zoom observation image, and the boundary setting section 340 that detects the position of a boundary on the normal observation image that corresponds to the boundary of the attention area specified on the zoom observation image based on the pixel values of the zoom observation image, and sets a boundary image at the detected position of the boundary (see FIG. 1).

The term "normal observation image" used herein refers to an image acquired by observation at a normal observation magnification, and the term "zoom observation image" used herein refers to an image acquired by observation at an observation magnification higher than the normal observation magnification. More specifically, the zoom observation image is an image that magnifies the image of the object within the observation area that is part of the normal observation image. The term "attention area" used herein refers to an area for which the user's observation priority is relatively higher than that of other areas. For example, when the user is a doctor, and desires to perform treatment, the attention area refers to an area that includes a mucosal area or a lesion area. If the doctor desires to observe bubbles or feces, the attention area refers to an area that includes a bubble area or a feces area. Specifically, the attention area for the user differs depending on the objective of observation, but is necessarily an area for which the user's observation priority is relatively higher than that of other areas. The term "boundary image" used herein refers to an image that indicates the boundary of the attention area. In the first embodiment, the position of the boundary is clearly presented to the user by setting the boundary image on the normal observation image. Note that the boundary may be presented to the user using an arbitrary method instead of setting the boundary image.

The above configuration makes it possible for the endoscopic image processing device that can acquire the normal observation image and the zoom observation image to specify the attention area from the zoom observation image, and set the boundary of the specified attention area on the normal observation image as the boundary image. This makes it possible to automatically reflect the information (e.g., information about the position of the boundary of the attention area) acquired from the zoom observation image in the normal observation image. Therefore, the user need not link the zoom observation image and the normal observation image. This reduces the burden imposed on the user, and allows the user to smoothly perform diagnosis and procedures. The zoom observation image is used to closely observe the object (e.g., accurately specify the attention area), and the normal observation image is used to perform procedures (e.g., excise the lesion area). Therefore, the user must perform diagnosis/procedures while appropriately switching the observation mode between zoom observation and normal observation. Accordingly, it is possible to significantly reduce the burden imposed on the user who uses the system by eliminating or reducing the need to link the normal observation image and the zoom observation image.

The boundary setting section 340 may detect the position of the boundary on the normal observation image based on the pixel values of the zoom observation image and the pixel values of the normal observation image.

This makes it possible to detect the position of the boundary on the normal observation image using the pixel values of the normal observation image in addition to the pixel values of the zoom observation image, so that an improvement in accuracy and the like can be implemented.

The boundary setting section 340 may include the observation area position detection section 341 (see FIG. 6) that detects the position of the observation area based on the pixel values of the zoom observation image and the pixel values of the normal observation image, the observation area being an area on the normal observation image. The boundary setting section 340 may detect the position of the boundary in the observation area based on the pixel values of the zoom observation image and the pixel values of the normal observation image. The observation area position detection section 341 may detect the position of the observation area by performing a matching process based on the pixel values of the zoom observation image and the pixel values of the normal observation image, for example.

The term "observation area" used herein refers to an area on the normal observation image that corresponds to the area observed using the zoom observation image.

Figures 13, 14:
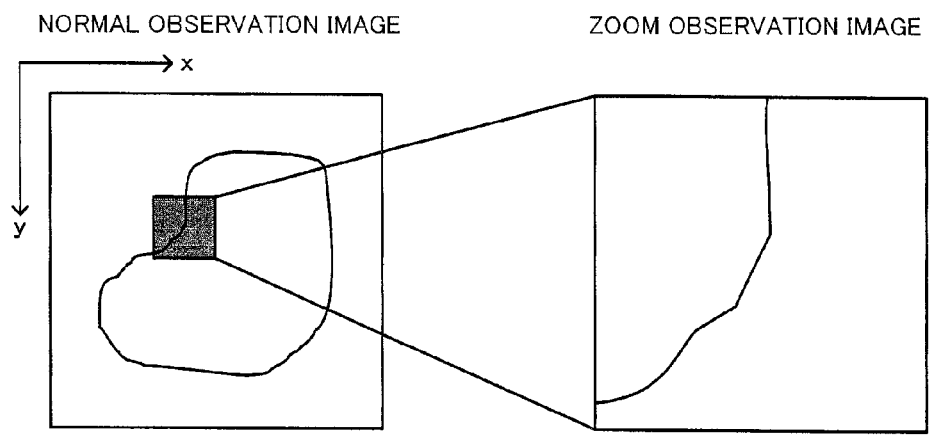
FIG. 13 is a view illustrating the relationship (link) between a normal observation image and a zoom observation image.
FIG. 14 illustrates an example of the data structure of observation area position information.

This makes it possible to determine the position on the normal observation image that corresponds to the area observed using the zoom observation image. When the normal observation image and the zoom observation image are linked as illustrated in FIG. 13 based on the pixel values of the normal observation image and the pixel values of the zoom observation image, the shaded area on the normal observation image is the observation area. The coordinates (i.e., the coordinates in the coordinate system illustrated in FIG. 13 of which the origin is the upper left corner of the normal observation image) of a reference point of the observation area and the size of the observation area (see FIG. 14) may be stored as the information about the position of the observation area, for example. The reference point may be the center point or the upper left corner of the observation area, for example. The information about the magnification during zoom observation may be stored instead of the size of the observation area. When the magnification during normal observation is 1, the magnification during zoom observation is Z, and the size of the normal observation image is M×N, the size of the observation area is M/Z×N/Z (when the normal observation image and the zoom observation image have an identical aspect ratio).

The normal observation image and the zoom observation image may be linked by a matching process, for example. Since the size of the observation area can be determined from the magnification Z during zoom observation, the matching process (e.g., block matching process) may be performed on the normal observation image and an image obtained by reducing the zoom observation image by 1/Z.

The boundary setting section 340 may include the motion information calculation section 344 that calculates the motion information that indicates the motion of the boundary detected on the normal observation image, and the boundary moving section 347 that moves the boundary image based on the calculated motion information (see FIG. 6).

This makes it possible to calculate the motion information that corresponds to the motion of the boundary that occurs due to the relative movement of the imaging section and the object or the like, and move the boundary (boundary image) corresponding to the motion information. Therefore, the boundary can be moved to follow the movement of the object (observation target) in the image, and displayed at an appropriate position.

The image acquisition section 320 may acquire a first normal observation image at a first timing, and acquire a second normal observation image at a second timing. The boundary setting section 340 may detect the position of the boundary on the first normal observation image, and set the boundary image. The motion information calculation section 344 may calculate the motion information that indicates the moving amount of the set boundary image between the first timing and the second timing. The boundary moving section 347 may calculate the position of the boundary on the second normal observation image based on the calculated motion information, and set the boundary image at the calculated position.

Figure 15:
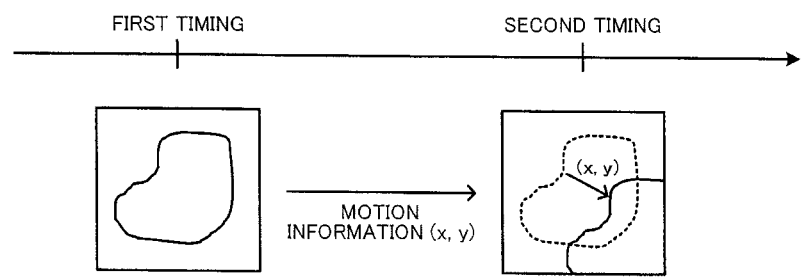
FIG. 15 is a view illustrating a method that moves a boundary when a zoom observation image is not acquired between a first timing and a second timing.

According to the above configuration, when the normal observation images have been acquired at the first timing and the second timing (see FIG. 15), the motion information that corresponds to the moving amount of the boundary between the first timing and the second timing is calculated. The position of the boundary can be specified at the second timing by moving the boundary at the first timing based on the calculated motion information. Therefore, even when the normal observation images have been acquired at two different timings, the position of the boundary at the latter timing can be specified from the boundary image at the former timing and the motion information.

The motion information calculation section 344 may calculate the motion information based on the first normal observation image and the second normal observation image. More specifically, the motion information calculation section 344 may calculate the motion information based on the motion vector between the first normal observation image and the second normal observation image.

This makes it possible to calculate the motion information about the motion between the first normal observation image and the second normal observation image based on the first normal observation image and the second normal observation image. For example, the above configuration may be applied to the case where the zoom observation image is not acquired between the first timing and the second timing. The above configuration may also be applied to the case where the first timing and the second timing are successive timings or the like, for example.

The image acquisition section 320 may successively acquire a plurality of the zoom observation images between the first timing and the second timing. The motion information calculation section 344 may calculate the motion information based on the motion of a corresponding reference point on the first normal observation image that corresponds to a reference point within the zoom observation image. For example, the motion information calculation section 344 may calculate the motion information based on the position of the corresponding reference point that corresponds to the reference point within a zoom observation image among the plurality of zoom observation images that has been acquired first, and the position of the corresponding reference point that corresponds to the reference point within a zoom observation image among the plurality of zoom observation images that has been acquired last.

Figure 16:
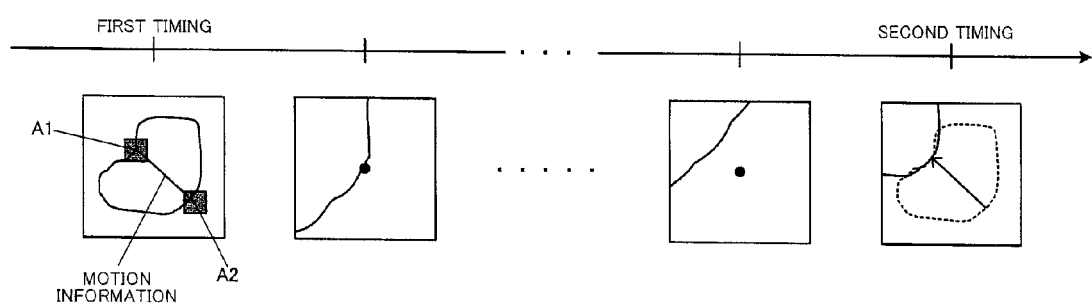
FIG. 16 is a view illustrating a method that moves a boundary when a zoom observation image is acquired between a first timing and a second timing.

This makes it possible to implement the process illustrated in FIG. 16. In FIG. 16, the center point of the zoom observation image is used as the reference point. Note that the reference point is not limited thereto. The corresponding reference point is indicated by A1 and A2 in FIG. 16. The motion information can be calculated from the corresponding reference point A1 that corresponds to the first zoom observation image and the corresponding reference point A2 that corresponds to the last zoom observation image. In the example illustrated in FIG. 16, since the imaging section has moved in the lower right direction (from A1 to A2), the boundary moves in the upper left direction by the motion amount. Therefore, the motion information about the motion between the normal observation images can be appropriately calculated even when the zoom observation image is acquired between the normal observation images. In the example illustrated in FIG. 16, since the first normal observation image and the second normal observation image are acquired at a long time interval, a deterioration in accuracy may occur when the motion amount is calculated directly from the first normal observation image and the second normal observation image. However, since it is difficult to calculate the motion amount between the normal observation image and the zoom observation image, it is impossible to calculate the motion amount between successive timings, and calculate the sum. The above problem can be solved by calculating the motion amount using the first zoom observation image and the last zoom observation image.

The boundary setting section 340 may include the boundary, update section 346 that updates the setting position of the boundary image on the normal observation image based on the information about the attention area on the zoom observation image (see FIG. 6).

This makes it possible to update the boundary image set on the normal observation image using the information about the zoom observation image, and link the zoom observation image and boundary of the not trial observation image.

The boundary update section 346 may perform a first determination process, and the attention area determination section 330 may perform a second determination process. The boundary update section 346 may update the setting position of the boundary image in the observation area based on the first determination process and the second determination process, the observation area being an area on the normal observation image that corresponds to the area observed using the zoom observation image.

The first determination process is a process that determines whether or not the observation area is close to the boundary image set on the normal observation image. The second determination process is a process that determines whether or not the observation area is the attention area. More specifically, the attention area determination section 330 may determine whether or not the observation area is the attention area based on the pixel values of the zoom observation image that corresponds to the observation area.

The boundary image may be updated based on the first determination process and the second determination process as described below, for example. When it has been determined by the first determination process that the observation area is close to the boundary image, and it has been determined by the second determination process that the observation area is the attention area, the setting position of the boundary image is updated so that the area of the figure enclosed by the boundary image increases (see FIG. 8D). When it has been determined by the first determination process that the observation area is close to the boundary image, and it has been determined by the second determination process that the observation area is a non-attention area, the setting position of the boundary image is updated so that the area of the figure enclosed by the boundary image decreases (see FIG. 8B).

This makes it possible to update the setting position of the boundary image based on the information about the zoom observation image that is close to (but need not necessarily come in contact with) the boundary image set on the normal observation image. Therefore, the detailed information about the object obtained by zoom observation can be appropriately reflected in the normal observation image, and the user (doctor) can smoothly perform diagnosis and procedures.

The boundary update section 346 may select a point on the boundary image set on the normal observation image as a control point, and determine whether or not the observation area is close to the control point as the first determination process. The attention area determination section 330 may determine whether or not the observation area is the attention area as the second determination process. The boundary update section 346 may update the setting position of the boundary image by updating the position of the control point close to the observation area based on the first determination process and the second determination process.

This makes it possible to update the setting position of the boundary image as illustrated in FIGS. 8A to 8D. In FIGS. 8A to 8D, the points indicated by "x" correspond to the control point. The control points are set along the boundary of the attention area at equal intervals (see FIG. 7B). Note that the control points need not necessarily be set at equal intervals. It is possible to reduce the amount of calculation and facilitate the process by thus updating the boundary image by updating the discrete control points instead of updating the entire boundary.

The endoscopic image processing device may include the observation candidate area setting section 3481 that sets a plurality of observation candidate areas on the normal observation image, the observation candidate area being an area that is a candidate for the observation area, the observation priority setting section 3482 that sets observation priority to each of the plurality of observation candidate areas, the observation priority indicating zoom observation priority, and the observation area selection section 3483 that selects the next observation target observation area based on the set observation priority (see FIG. 9).

The observation candidate areas are set as illustrated in FIG. 10, for example. In the example illustrated in FIG. 10, the observation candidate areas are set at positions corresponding to the control points. Note that the observation candidate areas may be set at arbitrary positions.

This makes it possible to set the observation candidate area that is a candidate for the observation area (i.e., an area on the normal observation image that corresponds to the area observed by zoom observation), and select the next observation target area. Therefore, the entire attention area can be efficiently observed by appropriately setting the observation priority, and observing the selected area.

The observation priority setting section 3482 may set first observation priority based on distance information about the distance from the zoom observation completion area to the observation candidate area, the zoom observation completion area indicating a range that has been subjected to zoom observation. The observation priority setting section 3482 may set second observation priority based on distance information about the distance from the observation area that indicates the current observation point to the observation candidate area, the observation area indicating the current observation point.

According to the above configuration, when the current observation area, the observation candidate areas, and the zoom observation completion area are set as illustrated in FIG. 12, the first observation priority can be set based on the distance information about the distance from the zoom observation completion area (see B1 in FIG. 12), and the second observation priority can be set based on the distance information about the distance from the observation area (see B2 in FIG. 12). For example, the observation candidate area that has not been sufficiently subjected to zoom observation and is close to the current observation point can be selected as the observation area by increasing the first observation priority as the distance from the zoom observation completion area increases, and increasing the second observation priority as the distance from the observation area decreases. Specifically, since an area that has not been sufficiently subjected to zoom observation and is close to the current observation point can be preferentially observed, the entire attention area can be efficiently observed.

The endoscopic image processing device may include the observation direction information output section 3484 that outputs the direction information about the direction from the observation area to the selected observation candidate area (see FIG. 12).

This makes it possible to output the direction information about direction from the current observation point (observation area) to the selected observation candidate area as an arrow or like (see FIG. 12). Therefore, the next observation target area can be clearly presented to the user.

The attention area determination section 330 may specify the attention area based on the pixel values of the pixels within the zoom observation image. More specifically, the attention area determination section 330 may specify the attention area based on the pixel values of the pixels within the zoom observation image and a reference value that is used as a reference for detecting the attention area.

According to the above configuration, since the attention area can be specified based on the pixel values of the pixels within the zoom observation image, the system can automatically specify the attention area.

The attention area determination section 330 may include the observation method determination section 331 that determines the observation method for the zoom observation image (see FIG. 3). The attention area determination section 330 may set the reference value corresponding to the determined observation method.

The observation method may include special light observation, for example.

This makes it possible to appropriately set the reference value corresponding to the observation method, and improve the attention area determination accuracy.

The attention area determination section 330 may include the feature quantity calculation section 3322 that calculates the feature quantity that is compared with the reference value based on the pixel values of the pixels within the zoom observation image (see FIG. 4). The attention area determination section 330 may specify the attention area based on the result of comparison between the feature quantity and the reference value.

This makes it possible to calculate the feature quantity based on the pixel values of the pixels within the zoom observation image. Since the feature quantity that shows a value specific to the attention area is used instead of directly using the pixel values of the pixels, the attention area determination accuracy can be improved.

The attention area determination section 330 may include the image division section 3321 that divides the zoom observation image into a plurality of blocks (see FIG. 4). The feature quantity calculation section 3322 may calculate the feature quantity on a block basis, and the attention area determination section 330 may specify the attention area by comparing the feature quantity with the reference value on a block basis.

According to the above configuration, the zoom observation image is divided into a plurality of blocks, and the feature quantity is calculated and compared with the reference value on a block basis. Since the attention area can be specified on a block basis, the attention area determination accuracy can be improved.

The first embodiment also relates to a program that causes a computer to function as the image acquisition section 320 that acquires a normal observation image and a zoom observation image, the attention area determination section 330 that specifies an attention area on the zoom observation image, and the boundary setting section 340 that detects the position of a boundary on the normal observation image that corresponds to the boundary of the attention area specified on the zoom observation image based on the pixel values of the zoom observation image, and sets a boundary image at the position of the detected boundary.

This makes it possible to apply the first embodiment to a system (e.g., imaging apparatus and endoscope system) that acquires an image, and processes the image, and a system that stores image data, and processes the stored image data by software using a computer system (e.g., PC), for example. The program is stored in an information storage device. The information storage device may be an arbitrary recording medium that is readable by an information processing device, such as an optical disk (e.g., DVD and CD), a magnetooptical disk, a hard disk (HDD), and a memory (e.g., nonvolatile memory and RAM).

3. Second Embodiment

Figure 17:
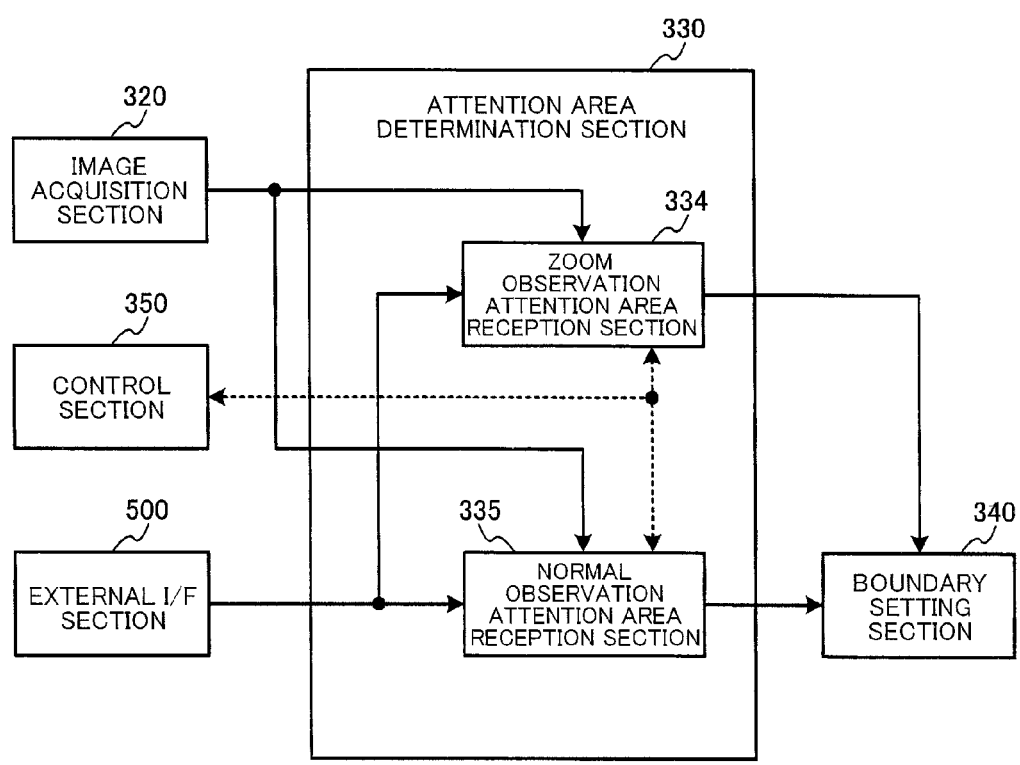
FIG. 17 illustrates another configuration example of an attention area determination section.

The configuration according to the second embodiment is the same as the configuration according to the first embodiment, except for the attention area determination section 330. A specific configuration of the attention area determination section 330 according to the second embodiment is described below. FIG. 17 is a block diagram illustrating an example of the configuration of the attention area determination section 330 according to the second embodiment. As illustrated in FIG. 17, the attention area determination section 330 includes a zoom observation attention area reception section 334 and a normal observation attention area reception section 335.

The zoom observation attention area designated by the user using the external I/F section 500 is output to the zoom observation attention area reception section 334 as a zoom observation designated attention area. The normal observation attention area designated by the user using the external I/F section 500 is output to the normal observation attention area reception section 335 as a normal observation designated attention area. The zoom observation attention area reception section 334 is connected to the boundary setting section 340. The normal observation attention area reception section 335 is also connected to the boundary setting section 340.

Figure 18:
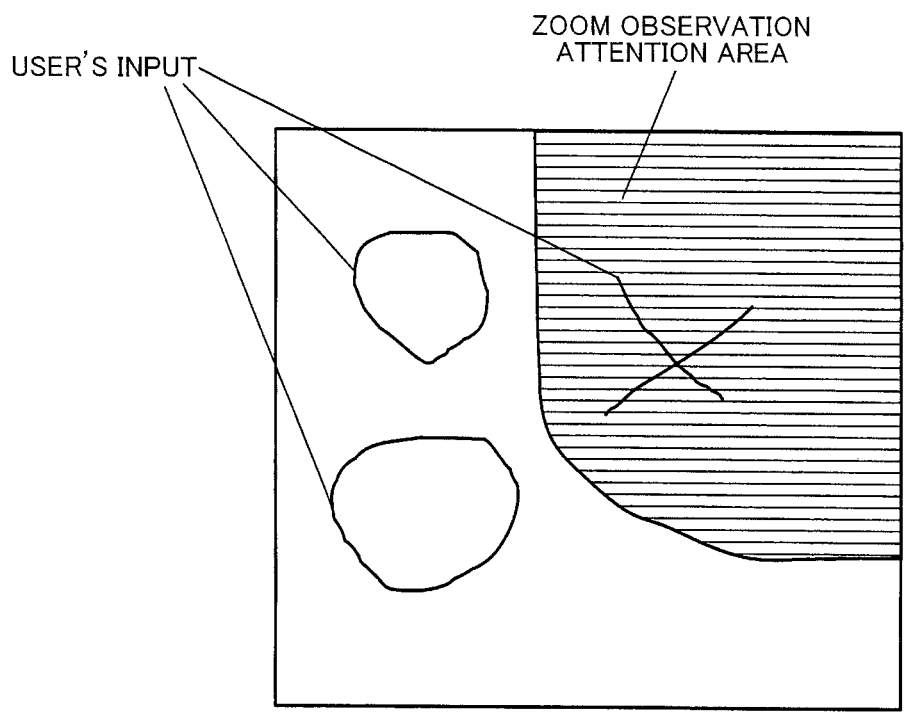
FIG. 18 illustrates an example in which an attention area and a non-attention area are input by the user during zoom observation.

The zoom observation attention area reception section 334 receives the zoom observation attention area designated by the user as the zoom observation designated attention area. For example, the external I/F section 500 includes a touch panel included in the endoscope monitor. The user can input the zoom observation attention area as the zoom observation designated attention area during zoom observation by touching the touch panel using a touch pen in an area that appears to be the zoom observation attention area. The external I/F section 500 that allows the user to input the zoom observation designated attention area may be an eye tracking device that detects the line of sight of the user, a mouse, or the like. For example, the user inputs (sets) the zoom observation designated attention area by drawing "x" in the attention area, and drawing "O" in the non-attention area (see FIG. 18). The user may input the zoom observation designated attention area by drawing (inputting) the boundary between the attention area and the non-attention area.

Figure 19A:
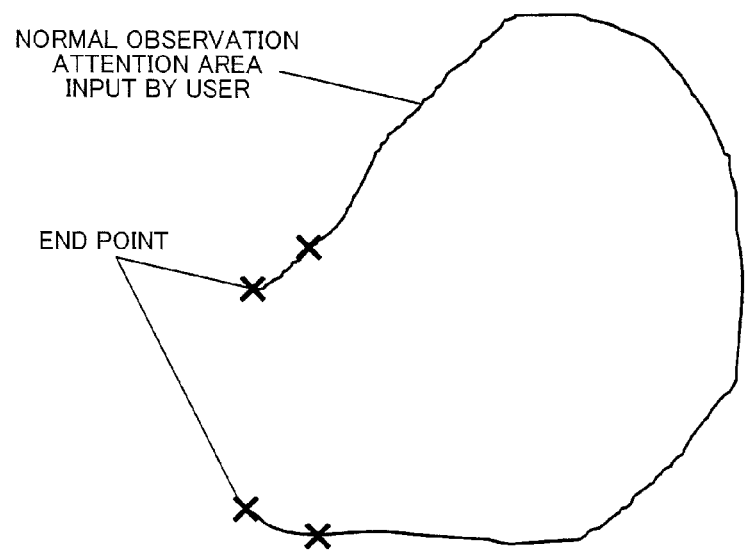
FIGS. 19A and 19B illustrate an example in which an attention area is input by the user during normal observation.
Figure 19B:
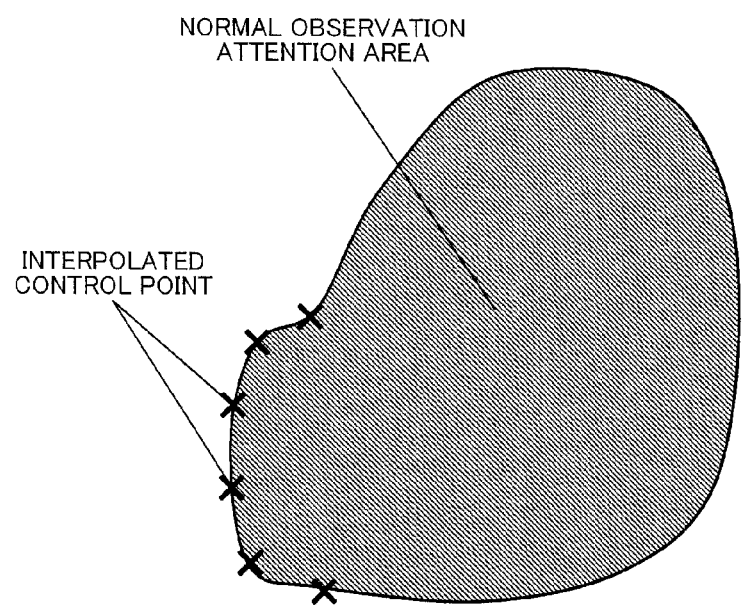

The normal observation attention area reception section 335 receives the normal observation attention area designated by the user as the normal observation designated attention area. For example, the external I/F section 500 includes a touch panel included in the endoscope monitor. The user can input the normal observation attention area as the normal observation designated attention area during normal observation by touching the touch panel using a touch pen in an area that appears to be the normal observation attention area. The external I/F section 500 that allows the user to input the normal observation designated attention area may be an eye tracking device that detects the line of sight of the user, a mouse, or the like. For example, the user inputs the normal observation designated attention area as illustrated in FIG. 19A. When the input normal observation designated attention area is an open curve, a correction process is performed so that the normal observation designated attention area becomes a closed curve. More specifically, control points are set on the open curve that forms the normal observation designated attention area at constant intervals. Note that the control points are necessarily set at the end points of the curve point. As illustrated in FIG. 19B, control points are interpolated by spline interpolation from the control points set at the end points of the curve point and the control points adjacent thereto, and the inner area of the closed curve is set as the normal observation attention area.

According to the second embodiment, the attention area determination section 330 receives attention area designation information that has been input by the user and specifies the attention area, and specifies the attention area based on the attention area designation information.

This makes it possible for the user to manually specify the attention area instead of causing the system to automatically detect the attention area.

The first and second embodiments according to the invention have been described above. Note that the invention is not limited to the first and second embodiments. Various modifications and variations may be made of the elements described in connection with the first and second embodiments without departing from the scope of the invention. A plurality of elements described in connection with the first or second embodiment may be appropriately combined to implement various configurations. For example, some of the elements described in connection with the first or second embodiment may be omitted. The elements described in connection with different embodiments may be appropriately combined. Specifically, various modifications and applications are possible without materially departing from the novel teachings and advantages of the invention.

REFERENCE SIGNS LIST

100: light source section, 110: white light source, 120: rotary filter, 130: condenser lens, 200: insertion section, 210: light guide fiber, 220: illumination lens, 230: objective lens, 240: image sensor, 300: signal processing section, 310: A/D conversion section, 320: image acquisition section, 330: attention area determination section, 331: observation method determination section, 332: zoom observation attention area detection section, 333: normal observation attention area detection section, 334: zoom observation attention area reception section, 335: normal observation attention area reception section, 340: boundary setting section, 341: observation area position detection section, 342: zoom observation result storage section, 343: boundary candidate setting section, 344: motion information calculation section, 345: zoom observation result moving section, 346: boundary update section, 347: boundary moving section, 348: observation direction setting section, 350: control section, 400: output section, 500: external I/F section, 3321: image division section, 3322: feature quantity calculation section, 3323: reference value acquisition section, 3324: feature quantity comparison section, 3481: observation candidate area setting section, 3482: observation priority setting section, 3483: observation area selection section, 3484: observation direction information output section

What is claimed is:

1. An endoscopic image processing device comprising:
    an image acquisition section that acquires a normal observation image and a zoom observation image, the normal observation image being an image that includes an image of an object, and the zoom observation image being an image that magnifies the image of the object within an observation area that is part of the normal observation image;
    an attention area determination section that specifies an attention area on the zoom observation image, the attention area being an area that requires attention; and
    a boundary setting section that detects a position of a boundary on the normal observation image that corresponds to a boundary of the attention area specified on the zoom observation image based on pixel values of the zoom observation image, and sets a boundary image at the detected position of the boundary on the normal observation image, the boundary image indicating the boundary of the attention area.

2. The endoscopic image processing device as defined in claim 1,
    the boundary setting section detecting the position of the boundary on the normal observation image based on the pixel values of the zoom observation image and pixel values of the normal observation image.

3. The endoscopic image processing device as defined in claim 2,
    the boundary setting section including an observation area position detection section that detects a position of the observation area on the normal observation image based on the pixel values of the zoom observation image and the pixel values of the normal observation image, the observation area being an area on the normal observation image that corresponds to an area observed using the zoom observation image, and
    the boundary setting section detecting the position of the boundary in the observation area based on the pixel values of the zoom observation image and pixel values of the normal observation image.

4. The endoscopic image processing device as defined in claim 3,
    the observation area position detection section detecting the observation area on the normal observation image by performing a matching process based on the pixel values of the zoom observation image and the pixel values of the normal observation image.

5. The endoscopic image processing device as defined in claim 1,
    the boundary setting section including:
        a motion information calculation section that calculates motion information that indicates a motion of the boundary detected on the normal observation image; and
        a boundary moving section that moves the boundary image set at the position of the boundary based on the calculated motion information about the boundary.

6. The endoscopic image processing device as defined in claim 5,
    the image acquisition section acquiring a first normal observation image at a first timing, and acquiring a second normal observation image at a second timing,
    the boundary setting section detecting the position of the boundary on the first normal observation image, and setting the boundary image at the detected position of the boundary,
    the motion information calculation section calculating the motion information that indicates a moving amount of the boundary detected on the first normal observation image between the first timing and the second timing, and the boundary moving section calculating the position of the boundary on the second normal observation image that corresponds to the position of the boundary detected on the first normal observation image based on the calculated motion information, and setting the boundary image at the calculated position of the boundary.

7. The endoscopic image processing device as defined in claim 6,
the motion information calculation section calculating the motion information based on the first normal observation image and the second normal observation image.

8. The endoscopic image processing device as defined in claim 7,
the motion information calculation section calculating the motion information based on a motion vector between the first normal observation image and the second normal observation image.

9. The endoscopic image processing device as defined in claim 6,
the image acquisition section successively acquiring a plurality of zoom observation images between the first timing and the second timing, the plurality of zoom observation images corresponding to an image that magnifies the image of the object within the observation area that is part of the first normal observation image, and
the motion information calculation section calculating the motion information about the boundary based on a motion of a corresponding reference point on the first normal observation image that corresponds to a reference point within the zoom observation image.

10. The endoscopic image processing device as defined in claim 9,
the motion information calculation section calculating the motion information about the boundary based on a position of the corresponding reference point on the first normal observation image that corresponds to the reference point within a zoom observation image among the plurality of zoom observation images that has been acquired first, and a position of the corresponding reference point on the first normal observation image that corresponds to the reference point within a zoom observation image among the plurality of zoom observation images that has been acquired last.

11. The endoscopic image processing device as defined in claim 1,
the boundary setting section including a boundary update section that updates a setting position of the boundary image on the normal observation image based on information about the attention area on the zoom observation image.

12. The endoscopic image processing device as defined in claim 11,
the boundary update section determining whether or not the observation area is close to the boundary image set on the normal observation image as a first determination process, the observation area being an area on the normal observation image that corresponds to an area observed using the zoom observation image,
the attention area determination section determining whether or not the observation area is the attention area as a second determination process, and
the boundary update section updating the setting position of the boundary image in the observation area based on a result of the first determination process and a result of the second determination process.

13. The endoscopic image processing device as defined in claim 12,
the attention area determination section determining whether or not the observation area is the attention area based on the pixel values of the zoom observation image that corresponds to the observation area.

14. The endoscopic image processing device as defined in claim 12,
the boundary update section updating the setting position of the boundary image so that an area of a figure enclosed by the set boundary image increases when it has been determined by the first determination process that the observation area is close to the boundary image, and it has been determined by the second determination process that the observation area is the attention area.

15. The endoscopic image processing device as defined in claim 12,
the boundary update section updating the setting position of the boundary image so that an area of a figure enclosed by the set boundary image decreases when it has been determined by the first determination process that the observation area is close to the boundary image, and it has been determined by the second determination process that the observation area is not the attention area.

16. The endoscopic image processing device as defined in claim 12,
the boundary update section selecting a point on the boundary image set on the normal observation image as a control point, and determining whether or not the observation area is close to the control point as the first determination process,
the attention area determination section determining whether or not the observation area is the attention area as the second determination process, and
the boundary update section updating the setting position of the boundary image by updating a position of the control point close to the observation area based on a result of the first determination process and a result of the second determination process.

17. The endoscopic image processing device as defined in claim 1, further comprising:
an observation candidate area setting section that sets a plurality of observation candidate areas on the normal observation image, the observation candidate area being an area that is a candidate for the observation area;
an observation priority setting section that sets observation priority to each of the plurality of observation candidate areas, the observation priority indicating zoom observation priority of the observation candidate area; and
an observation area selection section that selects a next observation target observation area based on the set observation priority.

18. The endoscopic image processing device as defined in claim 17,
the observation priority setting section calculating distance information about a distance from a zoom observation completion area to a position of each of the plurality of observation candidate areas, and setting first observation priority as the observation priority based on the calculated distance information, the zoom observation completion area indicating a range of the normal observation image that has been subjected to zoom observation.

19. The endoscopic image processing device as defined in claim 17,
the observation priority setting section calculating distance information about a distance from the observation area that indicates a current observation point on the normal observation image to a position of each of the plurality of observation candidate areas, and setting second observation priority as the observation priority based on the calculated distance information.

20. The endoscopic image processing device as defined in claim 17, further comprising:
an observation direction information output section that outputs direction information that indicates a direction from the observation area that indicates a current observation point to the selected observation area.

21. The endoscopic image processing device as defined in claim 1,
the attention area determination section specifying the attention area based on pixel values of pixels within the zoom observation image.

22. The endoscopic image processing device as defined in claim 21,
the attention area determination section specifying the attention area based on the pixel values of the pixels within the zoom observation image and a reference value that is used as a reference for detecting the attention area.

23. The endoscopic image processing device as defined in claim 22,
the attention area determination section including an observation method determination section that determines an observation method for the zoom observation image, and
the attention area determination section setting the reference value corresponding to the determined observation method.

24. The endoscopic image processing device as defined in claim 23,
the observation method including special light observation.

25. The endoscopic image processing device as defined in claim 23,
the attention area determination section including a feature quantity calculation section that calculates a feature quantity that is compared with the reference value based on the pixel values of the pixels within the zoom observation image, and
the attention area determination section specifying the attention area based on a result of comparison between the feature quantity and the reference value.

26. The endoscopic image processing device as defined in claim 25,
the attention area determination section including an image division section that divides the zoom observation image into a plurality of blocks,
the feature quantity calculation section calculating the feature quantity on a block basis, and
the attention area determination section specifying the attention area by comparing the feature quantity with the reference value on a block basis.

27. The endoscopic image processing device as defined in claim 1,
the attention area determination section receiving attention area designation information that has been input by a user and specifies the attention area, and specifying the attention area based on the received attention area designation information.

28. A non-transitory computer-readable storage device with an executable program stored thereon, wherein the program instructs a computer to perform steps of:
acquiring a normal observation image and a zoom observation image, the normal observation image being an image that includes an image of an object, and the zoom observation image being an image that magnifies the image of the object within an observation area that is part of the normal observation image;
specifying an attention area on the zoom observation image, the attention area being an area that requires attention; and
detecting a position of a boundary on the normal observation image that corresponds to a boundary of the attention area specified on the zoom observation image based on pixel values of the zoom observation image, and setting a boundary image at the detected position of the boundary on the normal observation image, the boundary image indicating the boundary of the attention area.

29. An image processing method comprising:
acquiring a normal observation image and a zoom observation image, the normal observation image being an image that includes an image of an object, and the zoom observation image being an image that magnifies the image of the object within an observation area that is part of the normal observation image;
specifying an attention area on the zoom observation image, the attention area being an area that requires attention; and
detecting a position of a boundary on the normal observation image that corresponds to a boundary of the attention area specified on the zoom observation image based on pixel values of the zoom observation image, and setting a boundary image at the detected position of the boundary on the normal observation image, the boundary image indicating the boundary of the attention area.

* * * * *